(12) United States Patent
Laulicht et al.

(10) Patent No.: US 9,907,704 B2
(45) Date of Patent: Mar. 6, 2018

(54) QUICK-RELEASE ADHESIVE TAPES

(71) Applicants: The Brigham and Women s Hospital, Inc., Boston, MA (US); Massachusetts Institute of Technology, Cambridge, MA (US)

(72) Inventors: Bryan Laulicht, Cambridge, MA (US); Jeffrey M. Karp, Brookline, MA (US); Robert S. Langer, Newton, MA (US)

(73) Assignees: The Brigham and Women's Hospital, Inc., Boston, MA (US); Massachusetts Institute of Technology, Cambridge, MA (US)

(*) Notice: Subject to any disclaimer, the term of this patent is extended or adjusted under 35 U.S.C. 154(b) by 41 days.

(21) Appl. No.: 14/405,917

(22) PCT Filed: Jun. 6, 2013

(86) PCT No.: PCT/US2013/044558
§ 371 (c)(1),
(2) Date: Dec. 5, 2014

(87) PCT Pub. No.: WO2013/184944
PCT Pub. Date: Dec. 12, 2013

(65) Prior Publication Data
US 2015/0144259 A1 May 28, 2015

Related U.S. Application Data

(60) Provisional application No. 61/656,639, filed on Jun. 7, 2012.

(51) Int. Cl.
*B32B 7/12* (2006.01)
*A61F 13/02* (2006.01)
(Continued)

(52) U.S. Cl.
CPC .......... *A61F 13/024* (2013.01); *A61F 13/025* (2013.01); *A61F 13/0246* (2013.01);
(Continued)

(58) Field of Classification Search
CPC ...... B29C 65/5021; B32B 38/10; B32B 37/26
See application file for complete search history.

(56) References Cited

U.S. PATENT DOCUMENTS 3,991,754 A 11/1976 Gertzman
4,696,854 A 9/1987 Ethier
(Continued)

FOREIGN PATENT DOCUMENTS

DE 10 2004 033421 1/2006
EP 0630628 12/1994
(Continued)

OTHER PUBLICATIONS

International Search Report and Written Opinion dated Sep. 12, 2013 in international application No. PCT/US2013/044558, 8 pgs.
(Continued)

*Primary Examiner* — Victor S Chang
(74) *Attorney, Agent, or Firm* — Fish & Richardson P.C.

(57) ABSTRACT

Methods and compositions for securing to and removing adhesive tapes from substrates, e.g., delicate substrates such as skin, are described. The methods include providing an adhesive tape comprising an adhesive layer and a support layer in contact with the adhesive layer. A first adhesion level between the adhesive layer and the support layer is, or can be controlled to be, less than a second adhesion level between the adhesive layer and the substrate. The methods further include applying the adhesive tape to the substrate by contacting the adhesive layer to the substrate while the support layer remains in contact with the adhesive layer; and
(Continued)

removing the support layer from the substrate by separating the support layer from the adhesive layer.

8 Claims, 21 Drawing Sheets

(51) Int. Cl.
*B29C 65/50* (2006.01)
*B32B 37/26* (2006.01)
*B32B 38/10* (2006.01)
*C09J 7/02* (2006.01)
*A61F 13/00* (2006.01)
*A61F 13/15* (2006.01)

(52) U.S. Cl.
CPC ...... *A61F 13/0253* (2013.01); *A61F 13/0256* (2013.01); *A61F 13/0259* (2013.01); *A61F 13/0269* (2013.01); *B29C 65/5021* (2013.01); *B32B 37/26* (2013.01); *B32B 38/10* (2013.01); *C09J 7/0285* (2013.01); *A61F 2013/008* (2013.01); *A61F 2013/0071* (2013.01); *A61F 2013/00412* (2013.01); *A61F 2013/00676* (2013.01); *A61F 2013/00685* (2013.01); *A61F 2013/00702* (2013.01); *A61F 2013/00748* (2013.01); *A61F 2013/00804* (2013.01); *A61F 2013/00838* (2013.01); *A61F 2013/15569* (2013.01); *B32B 2037/268* (2013.01); *C09J 2205/302* (2013.01); *C09J 2467/006* (2013.01); *Y10T 428/24851* (2015.01); *Y10T 428/2839* (2015.01)

(56) References Cited

U.S. PATENT DOCUMENTS

| | | | |
|---|---|---|---|
| 5,449,540 | A | 9/1995 | Calhoun et al. |
| 5,709,651 | A | 1/1998 | Ward |
| 5,807,632 | A | 9/1998 | Pedginski et al. |
| 5,942,065 | A | 8/1999 | Biggs et al. |
| 6,388,231 | B1 | 5/2002 | Andrews |
| 6,551,285 | B1 | 4/2003 | Bierman |
| 6,828,018 | B2 | 12/2004 | Waterbury et al. |
| 7,431,985 | B2 | 10/2008 | Iwama |
| 7,897,226 | B2 | 3/2011 | Suzuki |
| 2006/0228480 | A1 | 10/2006 | Lin |
| 2007/0010777 | A1 | 1/2007 | Dunshee et al. |
| 2008/0286517 | A1 | 11/2008 | Zickell et al. |
| 2009/0061222 | A1 | 3/2009 | Grobe |
| 2010/0084084 | A1 | 4/2010 | Miller, II |
| 2011/0070391 | A1 | 3/2011 | Cotton |

FOREIGN PATENT DOCUMENTS

| | | |
|---|---|---|
| JP | S5470340 | 6/1979 |
| JP | H01240589 | 9/1989 |
| TW | 443966 | 7/2001 |
| WO | WO 1995/24238 | 9/1995 |
| WO | 2007/117208 | 10/2007 |
| WO | 2009/108884 | 9/2009 |
| WO | WO 2010/107543 | 9/2010 |
| WO | WO 2012/019721 | 2/2012 |
| ZA | 8601807 | 10/1987 |

OTHER PUBLICATIONS

Supplementary European Search Report in European Application No. EP 13 80 0636, dated Feb. 23, 2016, 5 pages.
Office Action in European Application No. EP 13 80 0636, dated Apr. 7, 2016, 7 pages.
International Preliminary Report on Patentability in International Application No. PCT/US2013/044558, dated Dec. 18, 2014, 6 pages.
Bartlett et al., "Looking Beyond Fibrillar Features to Scale Gecko-Like Adhesion," Adv Mater., 24:1078-1083 (2012).
Boesel et al., "A Path to Strong and Reversible Dry Adhesives" Adv Mater., 22:2125-2137 (May 18, 2010).
Gorb et al., "Insects did it first: a micropatterned adhesive tape for robotic applications," Bioinsp. Biomim., 2:S117-S125 (2007).
Jeong et al., "A nontransferring dry adhesive with hierarchical polymer nanohairs" PNAS, 106(14)5369-5644 (Apr. 7, 2009).
Lee et al., "Directional adhesion of gecko-inspired angled microfiber arrays" Appl Phys Lett., 93:191910-12 (2008).
Mandavi et al., "A biodegradable and biocompatible gecko-inspired tissue adhesive," PNAS, 105(7):2307-2312 (Feb. 19, 2008).
MED 2121U, "Solventless Acrylic Transfer Tape," 2 pages. (Feb. 2012).
Office Action in European Application No. 13800636.6, dated Feb. 8, 2017, 7 pages.

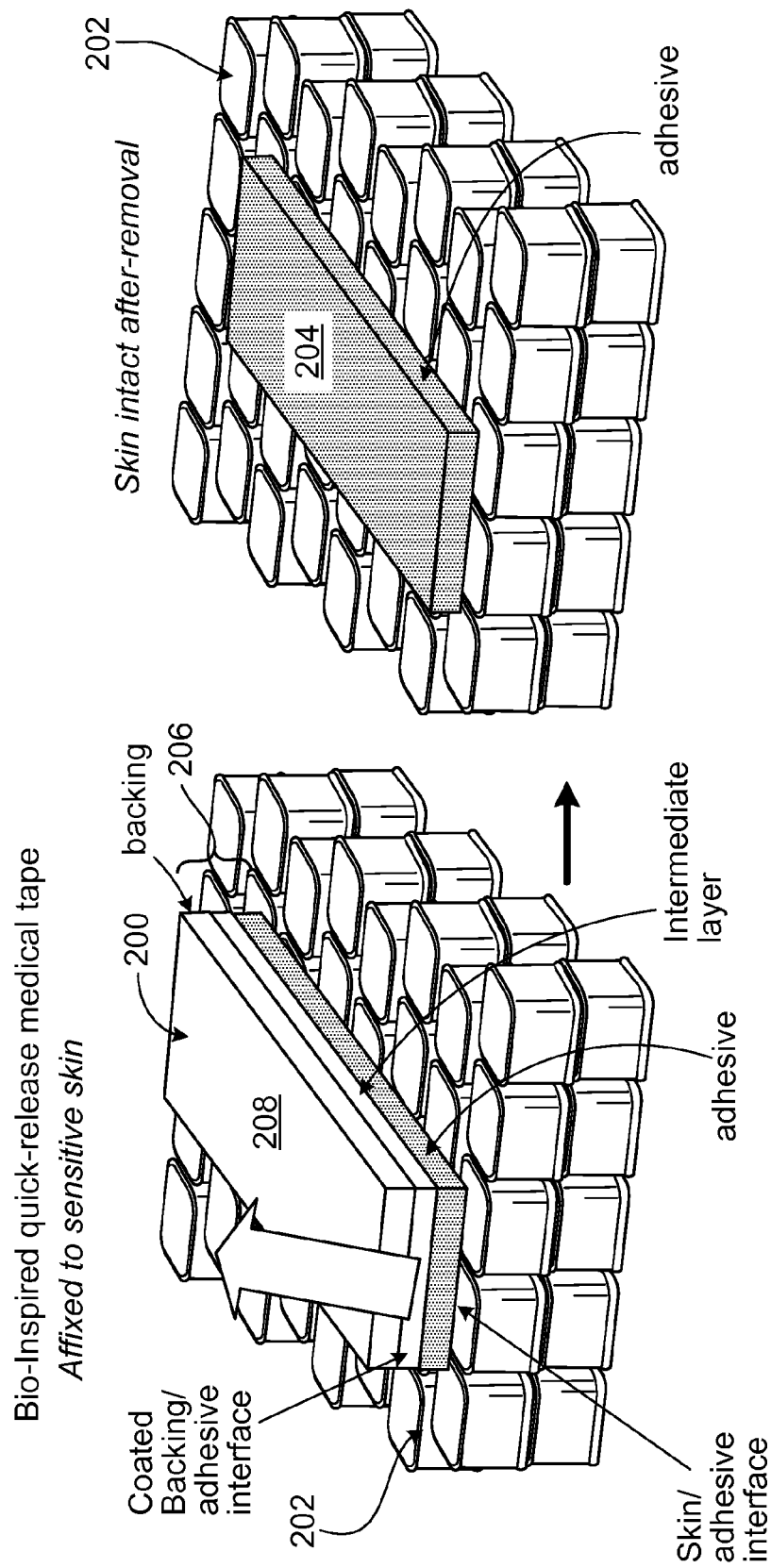

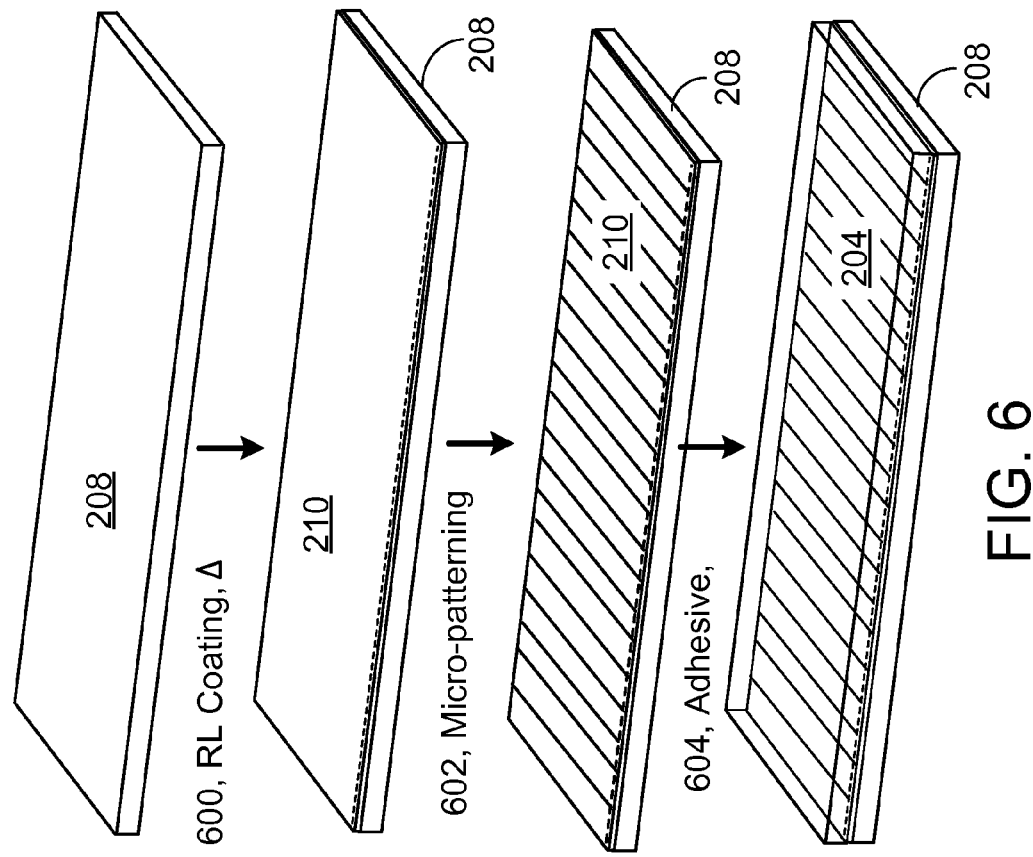
FIG. 6
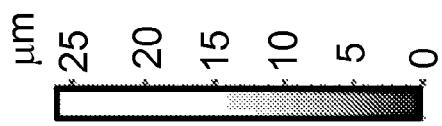
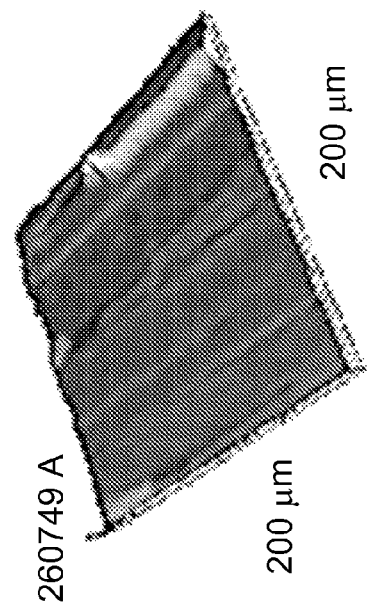
FIG. 5

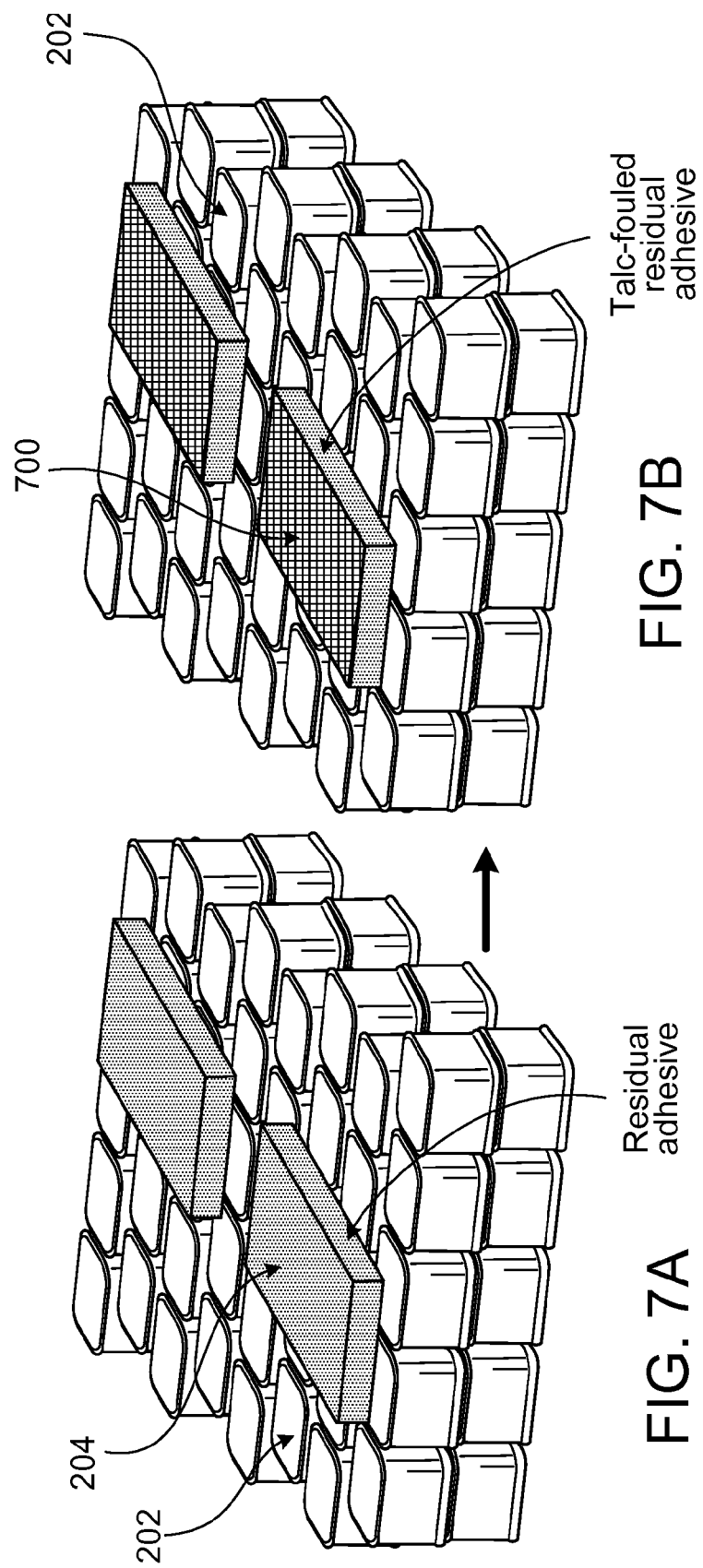

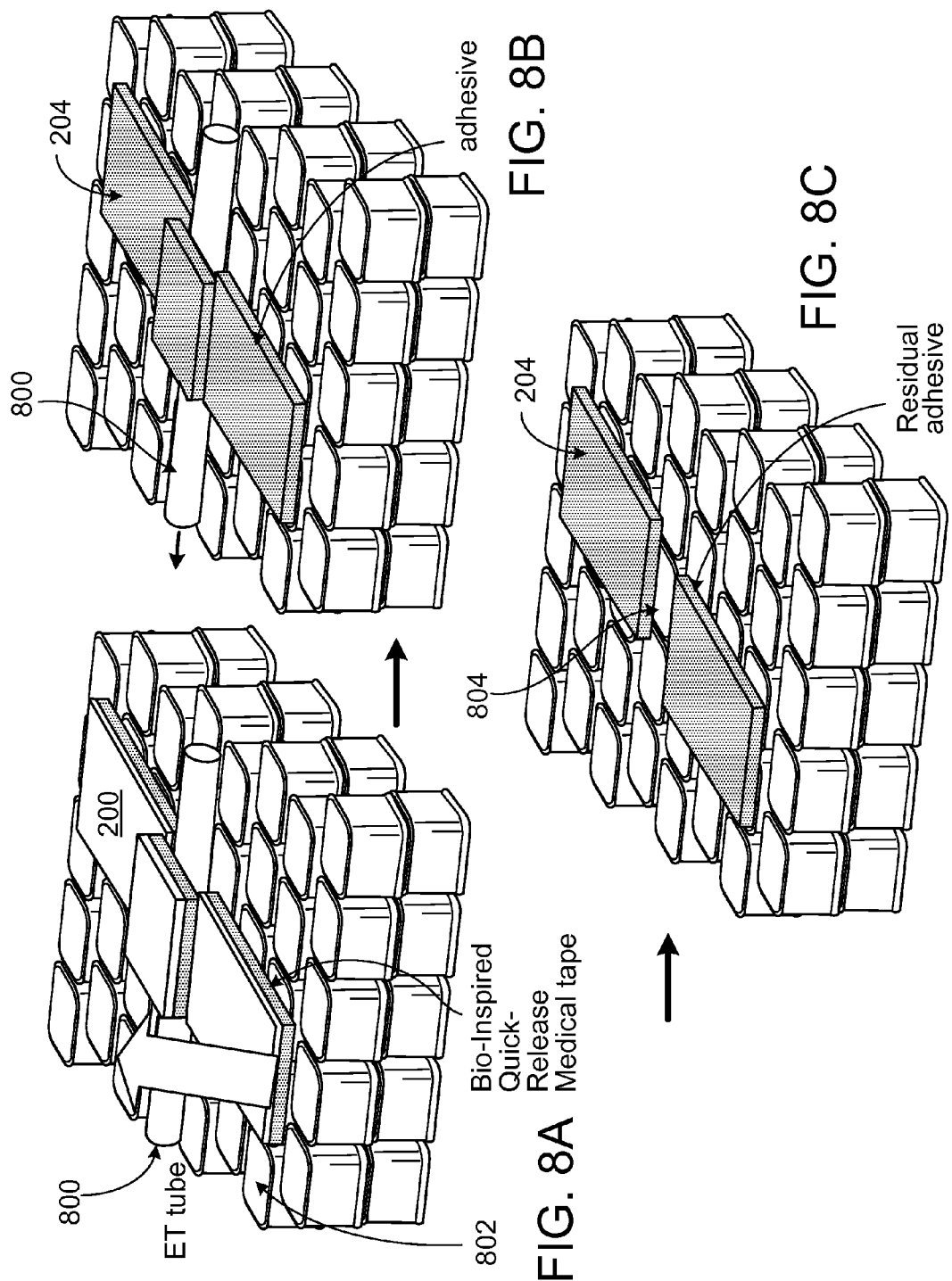

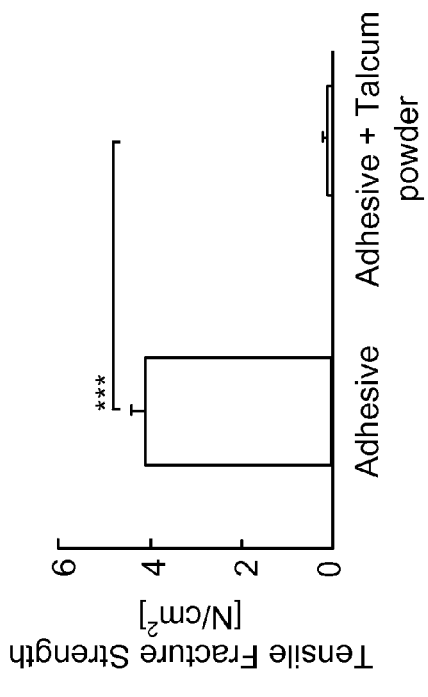
FIG. 21A
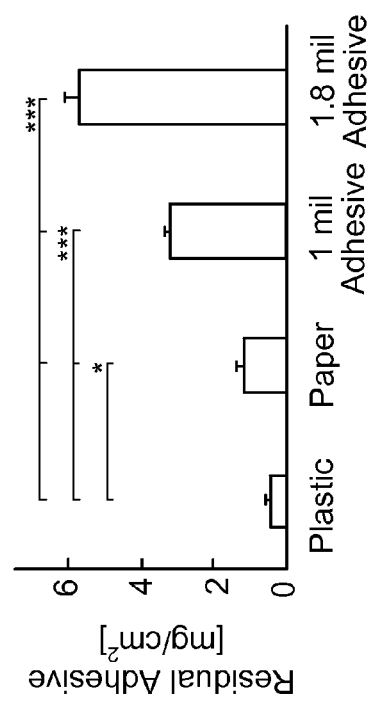
FIG. 21B
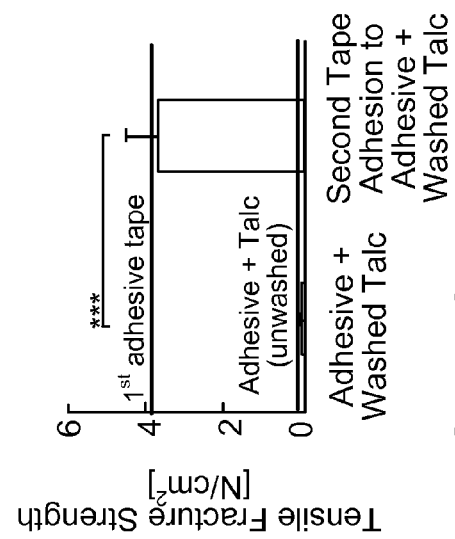
FIG. 21C
FIG. 21D

QUICK-RELEASE ADHESIVE TAPES

CLAIM OF PRIORITY

This application is a U.S. National Phase Application under 35 U.S.C. § 371 of International Patent Application No. PCT/US2013/044558, filed on Jun. 6, 2013, which claims priority to U.S. Provisional Application Ser. No. 61/656,639, filed on Jun. 7, 2012, the entire contents of which are hereby incorporated by reference.

STATEMENT AS TO FEDERALLY SPONSORED RESEARCH

This invention was made with Government support under Grant No. 106430 awarded by Philips Fund; and the National Institutes of Health Grant No. NIH OSP#6921553 NIH-DE013023. The Government has certain rights in the invention.

FIELD OF THE INVENTION

The invention relates to medical and other adhesive tapes.

BACKGROUND OF THE INVENTION

Medical adhesive removal causes more than 1.5 million injuries each year in the US alone. Neonatal skin lacks an epidermis, making it highly sensitive and prone to damage during adhesive tape removal. Injuries due to adhesive tape removal from neonates include skin irritation, permanent scarring, and lifelong restrictions of motion resulting, for instance, from fibrosis, which can occur near joints or other dynamic tissues injured by the removal of adhesive tapes. The removal of medical adhesive tapes is also dangerous to elderly subjects, whose skin is often thin and loosely anchored.

FIGS. 1A-1B show a conventional medical tape 100 affixed to skin 102, such as the sensitive skin of a neonate. Tape 100 is a bilayer tape that includes an adhesive 104 supported on a backing 106. When tape 100 is removed, portions of skin 102 remain attached to adhesive 104 and may be removed along with the tape; other portions of adhesive 104 stay on the skin as residual adhesive 108.

SUMMARY OF THE INVENTION

The invention is based, at least in part, on the discovery that quick-release tapes that have an adhesive layer and a support layer, arranged such that the support layer can be easily removed from the adhesive layer, can be quickly and easily removed from a substrate (e.g., delicate substrates such as skin, e.g., in elderly or neonatal subjects) without damaging the substrate, e.g., the skin, while all or most of the adhesive remains on the substrate. Removal of the support layer can be achieved, for instance, by causing the adhesion between the adhesive layer and the support layer to be less than the adhesion between the adhesive layer and the substrate.

In a general aspect, methods for securing to and removing from a substrate, e.g., skin, such as delicate skin, an adhesive tape includes providing an adhesive tape comprising an adhesive layer and a support layer in contact with the adhesive layer. A first adhesion level between the adhesive layer and the support layer is less than a second adhesion level between the adhesive layer and the substrate. The methods further include applying the adhesive tape to the substrate by contacting the adhesive layer to the substrate while the support layer remains in contact with the adhesive layer; and removing the adhesive tape by removing the support layer from the substrate by separating the support layer from the adhesive layer, and leaving the adhesive layer behind on the substrate.

In various implementations, these methods include one or more of the following features.

The first adhesion level is controlled during manufacture of the adhesive tape, and removing the support layer from the substrate includes peeling the support layer away from the adhesive layer.

Removing the support layer from the substrate includes controlling the first adhesion level to reduce the first adhesion level to be less than the second adhesion level and then peeling the support layer from the adhesive layer.

Removing the support layer from the substrate includes removing the support layer without damaging the substrate.

Removing the support layer from the substrate causes a device fixation shear adhesion characteristic of the adhesive tape to be reduced by at least about 25%, e.g., 50% or 75%.

Removing the support layer from the substrate includes applying a normal force to an interface between the support layer and the adhesive layer.

The adhesive layer can adhere to the substrate without removal of the support layer.

The support layer includes a backing, and a release agent layer disposed between the backing and the adhesive layer. The first adhesion level between the adhesive layer and the support layer is altered by a structural characteristic of the release agent layer. The structural characteristic includes discontinuities in the release agent layer. The structural characteristic includes a percent area of the backing that is exposed to the adhesive layer. A third adhesion level between the adhesive layer and the release agent layer is less than the second adhesion level between the adhesive layer and the substrate.

A force sufficient to separate the support layer from the adhesive layer is at least 10%, 50%, or 90% less than a force sufficient to remove at least a portion of the adhesive layer from the substrate.

Removing the support layer from the substrate includes leaving at least 75% or 90% of the adhesive layer on the substrate.

The methods further include causing the adhesive layer that remains on the substrate after removal of the adhesive tape to be de-tackified. Causing the adhesive layer to be de-tackified includes coating the adhesive layer with a powder. The method further includes adhering a second tape to the de-tackified adhesive layer.

Applying the adhesive tape to the substrate includes affixing a medical device to the substrate.

In another general aspect, quick-release tapes include a support layer, including a backing, and a patterned release agent layer disposed on the backing layer. The quick-release tapes also include an adhesive layer disposed on the release agent layer.

In various implementations, these tapes can include one or more of the following features.

The adhesive layer is configured to be disposed on a substrate. A first adhesion level between the adhesive layer and the substrate is greater than a second adhesion level between the adhesive layer and the support layer.

An adhesion level between the adhesive layer and the release agent layer is a function of an angle of a force applied to an interface between the adhesive layer and the release agent layer.

The patterned release agent layer can be patterned with an irregular pattern.

The release agent layer includes first domains and second domains. A first adhesion level between the first domains and the adhesive layer is different from a second adhesion level between the second domains and the adhesive layer. An adhesion level between the adhesive layer and the support layer is a function of a fraction of the release agent layer composed of the first domains. The adhesive layer is in contact with the backing in the first domains.

An adhesion level between the adhesive layer and the support layer is a function of a percent area of the backing that is exposed to the adhesive layer.

The release layer can be discontinuous.

The backing is formed of a first backing material having a first stiffness and a second backing material having a second stiffness less than the first stiffness.

The tapes further include a cover layer disposed on the adhesive layer. A first adhesion level between the cover layer and the support layer is less than a second adhesion level between the adhesive layer and the support layer.

The backing forms part of a medical device.

A first image is formed on the support layer. A second image is formed on the adhesive layer.

In another general aspect, methods for making a tape include forming a support layer by disposing a release agent layer onto a backing layer, and patterning the release agent layer. The methods also include disposing an adhesive layer onto the patterned release agent layer such that at least a portion of the adhesive layer contacts the backing layer.

In various implementations, these methods can include one or more of the following features.

Patterning the release agent layer includes removing a portion of the release agent layer. An adhesion level between the adhesive layer and the support layer is a function of a fraction of the release agent layer that is removed.

Patterning the release agent layer includes etching the release agent layer.

Patterning the release agent layer includes mechanically abrading the release agent layer.

Patterning the release agent layer includes forming first domains and second domains in the release agent layer. A first adhesion level between the first domains and the adhesive layer is different from a second adhesion level between the second domains and the adhesive layer. An adhesion between the adhesive layer and the support layer is a function of a fraction of the release agent layer composed of the first domains.

In another general aspect, quick-release tapes include a support layer, including a backing, and a release agent layer disposed on the backing layer. The tapes include an adhesive layer disposed on the release agent layer, and the release layer is formed of a material having an adhesion level that changes in response to a stimulus.

In various implementations, these tapes can include one or more of the following features.

The stimulus is an enzyme and the release agent layer includes a material that degrades in the presence of an enzyme.

The release agent layer includes a pH sensitive material and wherein the stimulus is the presence of a solution of a pH sufficient to dissolve the release agent layer.

The release agent layer includes a photodegradable material and wherein the stimulus is the presence of light.

The release agent layer includes a material that swells in response to the stimulus.

The release agent layer includes a shape memory material.

The adhesive layer is configured to be disposed on a substrate, wherein a first adhesion level between the adhesive layer and the substrate is greater than a second adhesion level between the adhesive layer and the support layer.

In another general aspect, quick release tapes include a support layer, including a backing, and a release agent layer disposed on the backing layer. The release agent layer includes a release modifying agent. The tapes include an adhesive layer disposed on the release agent layer.

In an embodiment, the release modifying agent can include a siloxane resin.

The quick-release tapes described herein have and provide a number of advantages. For instance, the tapes can be used to securely affix a device, such as a medical device, to a substrate, such as skin. The tapes securely retain the device and then, when desired, allow the device to be removed quickly, easily, and without damage to the underlying skin. Residual adhesive left on the skin after tape removal can be easily detackified, mitigating any risk that may have been presented by allowing adhesive to remain on the skin. In general, the quick-release tapes described herein are suitable for use in situations with a need for a strong adhesive, yet easily removable tape, such as for use with neonatal subjects, geriatric subjects, or other subjects with sensitive and/or delicate skin. In addition, a wide range of backing materials, release layers, and adhesives can be used to form the quick-release tapes, thus enabling the mechanical and biocompatibility characteristics of the tape to be engineered to suit a diverse array of situations. Furthermore, the quick-release tapes can be fabricated using scalable processes that are compatible with industrial infrastructure and processing.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 2A is a schematic diagram of a quick-release tape affixed to a portion of skin.

FIG. 2B is a schematic diagram of the portion of skin of FIG. 2A after removal of the quick-release tape.

FIG. 5 is a 3D optical profile of a release agent layer roughened by 400 grit sandpaper.

FIG. 6 is a schematic view of an example of a method of making a quick-release tape.

FIGS. 7A-7B are schematic diagrams of residual adhesive remaining on a portion of skin after removal of a support layer and after fouling with talcum powder, respectively.

FIG. 8A is a schematic diagram of a quick-release tape affixing an endotracheal (ET) tube to a portion of skin.

FIG. 8B is a schematic diagram of the portion of skin of FIG. 8A after removal of the backing of the quick-release tape.

FIG. 8C is a schematic diagram of the portion of skin of FIG. 8B after removal of the ET tube.

FIG. 21A is a schematic diagram of an experimental setup for a probe tack test.

FIG. 21B is a plot of the results of a probe tack test on residual adhesive and talcum powder fouled residual adhesive.

FIG. 21C is a plot of the results of a probe tack test on fouled, washed residual adhesive.

FIG. 21D is a plot of the residual adhesive mass per area after removal of the backing of a quick-release tape.

DETAILED DESCRIPTION

Figures 1A, 1B:
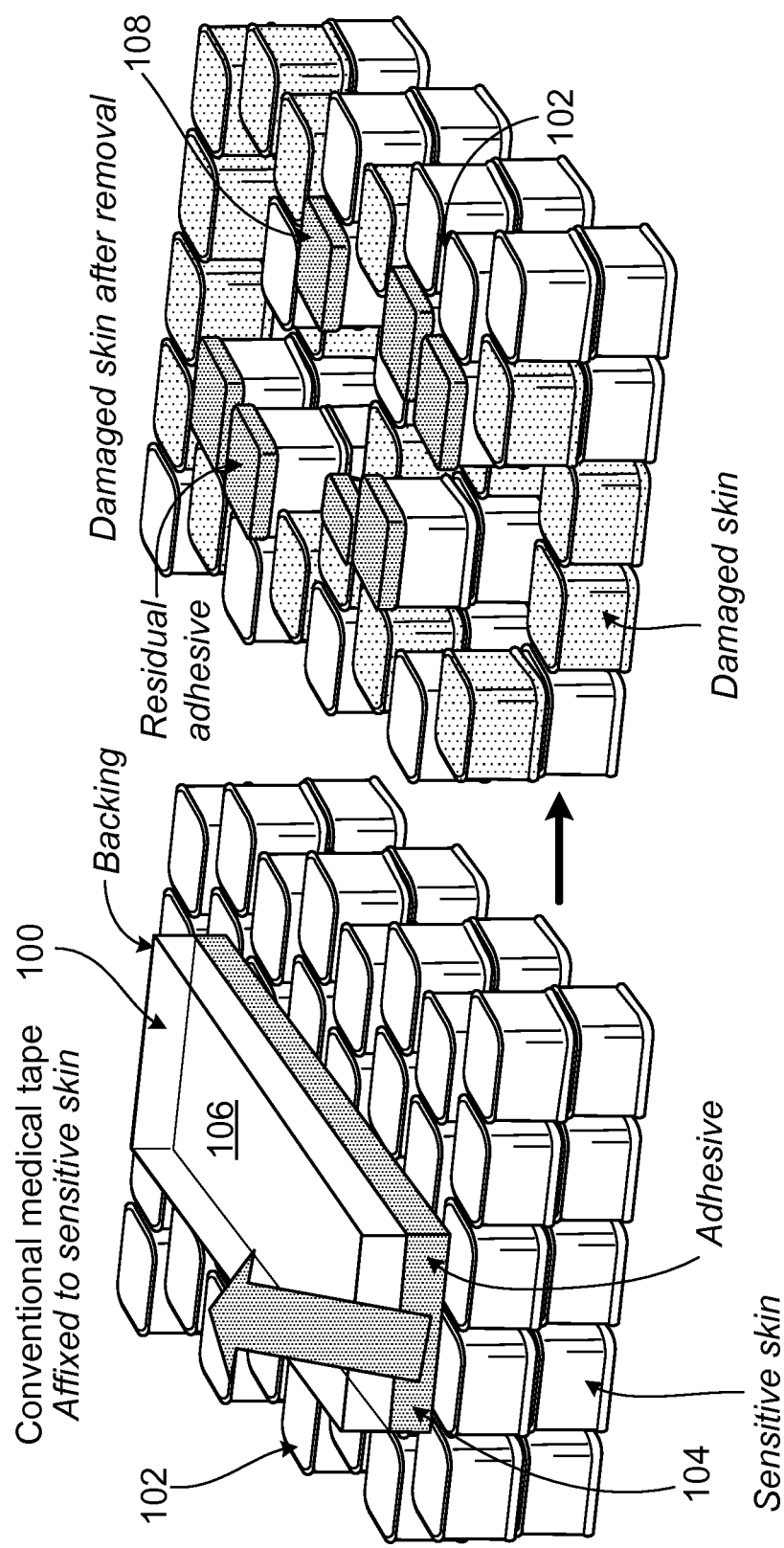
FIG. 1A is a schematic diagram of a conventional medical tape affixed to a portion of skin.
FIG. 1B is a schematic diagram of the portion of skin of FIG. 1A after removal of the conventional medical tape.

As shown in FIGS. 2A and 2B, an example of one embodiment of the new quick-release tapes 200 can be quickly and easily removed from a substrate 202 (e.g., skin) without damaging the substrate. Such a tape is useful, for instance, for affixing medical devices to subjects with delicate and/or sensitive skin, such as neonatal subjects, children, and elderly or geriatric subjects. Tape 200 includes an adhesive layer 204 and a support layer 206, arranged such that support layer 206 can be quickly and easily removed while leaving substantially all of adhesive layer 204 on substrate 202 (FIG. 2B). When tape 200 is used to affix a device to substrate 202, the device is strongly secured to the substrate. However, upon removal of support layer 206, the affixed device can be removed quickly and without damage to the substrate. Residual adhesive that remains on substrate 202 after removal of support layer 206 can be detackified by applying a powder, e.g., talcum powder, to the adhesive. Other tapes, including conventional tapes and quick-release tapes, can adhere to washed, talc-fouled residual adhesive, allowing another device to be affixed in a similar position as the previously removed device.

Support layer 206 can be easily removed from the adhesive layer by causing the adhesion between adhesive layer 204 and support layer 206 (e.g., the tendency of the adhesive layer to stick to the support layer, where the adhesion level is the degree of adhesion between the two layers) to be less than the adhesion between adhesive layer 204 and substrate 202. For instance, in some embodiments, support layer 206 includes two sub-layers: a backing 208 and a release agent layer 210. Backing 208 generally provides tape 200 with the majority of its cohesive mechanical strength; decoupling backing 208 from adhesive layer 204 prior to tape removal enables easy removal of support layer 206. One approach to decouple or separate backing 208 from adhesive layer 204 is to micro-pattern release agent layer 210. Because the surface area of interaction between backing 208 and adhesive layer 204 correlates with the peel force required to separate support layer 206 from adhesive layer 204, selective removal of portions of release agent layer 210 can be used to tune the adhesion between support layer 206 and adhesive layer 204 in a controllable, predictable manner, without sacrificing device fixation integrity.

General Structure of the Quick-Release Tapes

Figure 3:
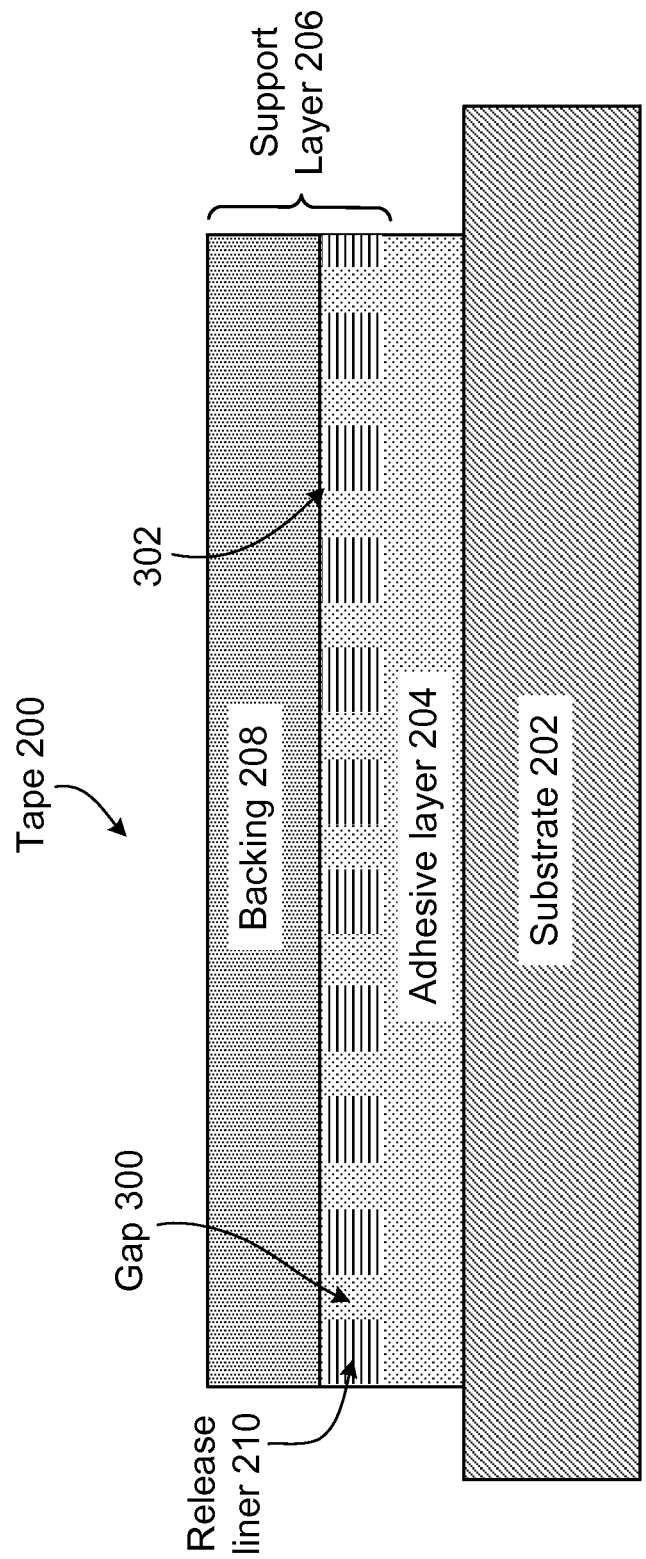
FIG. 3 is a cross-sectional view of a quick-release tape.

FIG. 3 illustrates an example of a quick-release tape 200 that includes an adhesive layer and a support layer 206. Support layer 206 is formed of a backing 208, which provides cohesive mechanical strength to tape 200; and a release agent layer 210, which allows for easy removal of support layer 206 from adhesive layer 204. Adhesive layer 204 is generally about 50 µm thick (e.g., 5, 25, or 1,000 µm); backing 208 is generally at least 50 µm thick (e.g., 10, 100, or 1,000 µm), and is generally thicker than the adhesive layer. Release agent layer 210 has a thickness ranging from about 0.5 µm to about 0.8 µm (e.g., 0.1, 50, or 750 µm).

The release agent layer can be designed so that the adhesion between adhesive layer 204 and release agent layer 210 is greater than the adhesion between release agent layer 210 and substrate 202. One of the ways in which this can be achieved is by micro-patterning the release agent layer. In other embodiments, the release agent layer can be made to dissolve or otherwise change so that it adheres less strongly to the support layer or completely disappears, allowing the adhesive layer to separate from the support layer.

Micro-patterning of release agent layer 210 removes material from the release agent layer, creating gaps 300. In some cases, the micro-patterned release agent layer is continuous (e.g., an uninterrupted pathway exists from one point in the release agent layer to any other point in the release agent layer). In other cases, the micro-patterned release agent layer is discontinuous (e.g., an uninterrupted pathway does not exist from one point in the release agent layer to at least one other point in the release agent layer). Because adhesive layer 204 is formed of a viscous, pressure-sensitive adhesive, once adhesive layer 204 is disposed onto release agent layer 210, as described below, adhesive flows into gaps 300 and comes into contact with backing 208.

Figure 4A:
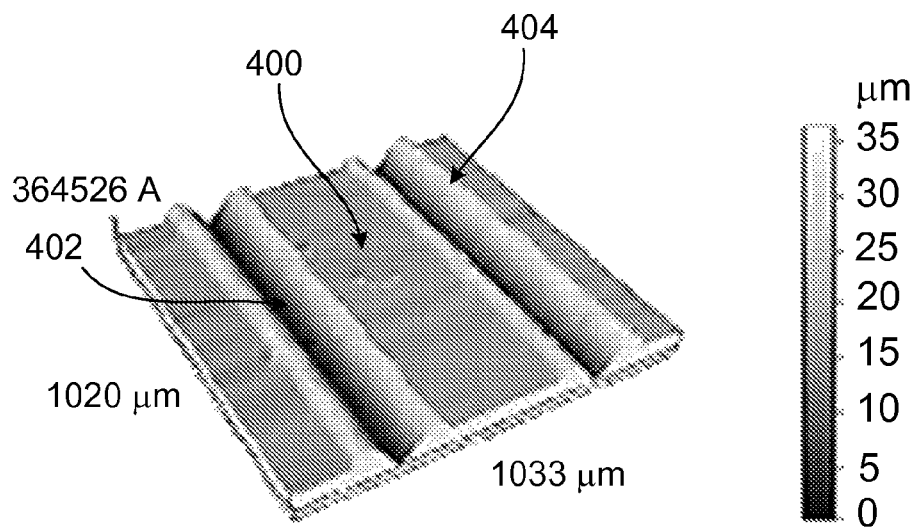
FIGS. 4A-4B are three-dimensional (3D) and two-dimensional (2D) profiles, respectively, of laser-etched lines in a release agent layer of a quick-release tape.
Figure 4B:
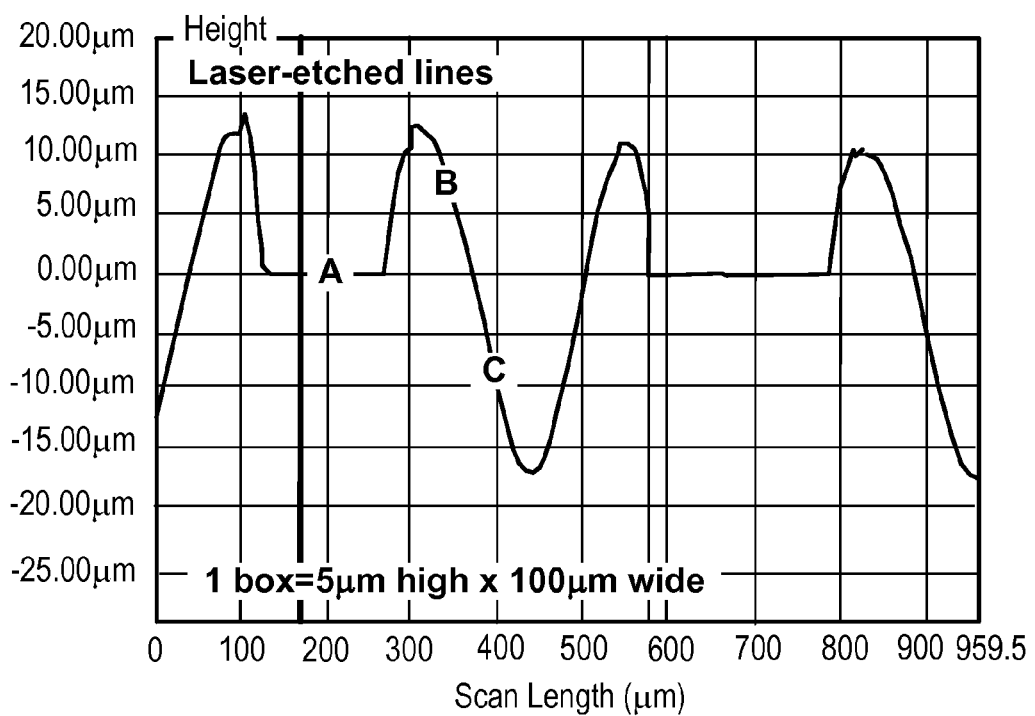
Figure 4C:
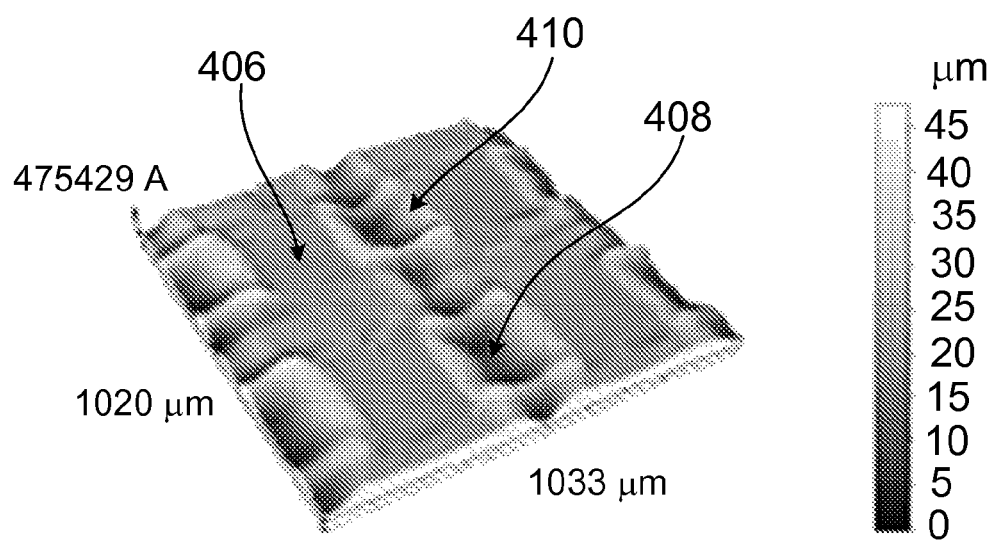
FIGS. 4C-4D are 3D and 2D optical profiles, respectively, of laser-etched grid lines, of laser-etched lines in a release agent layer of a quick-release tape.
Figure 4D:
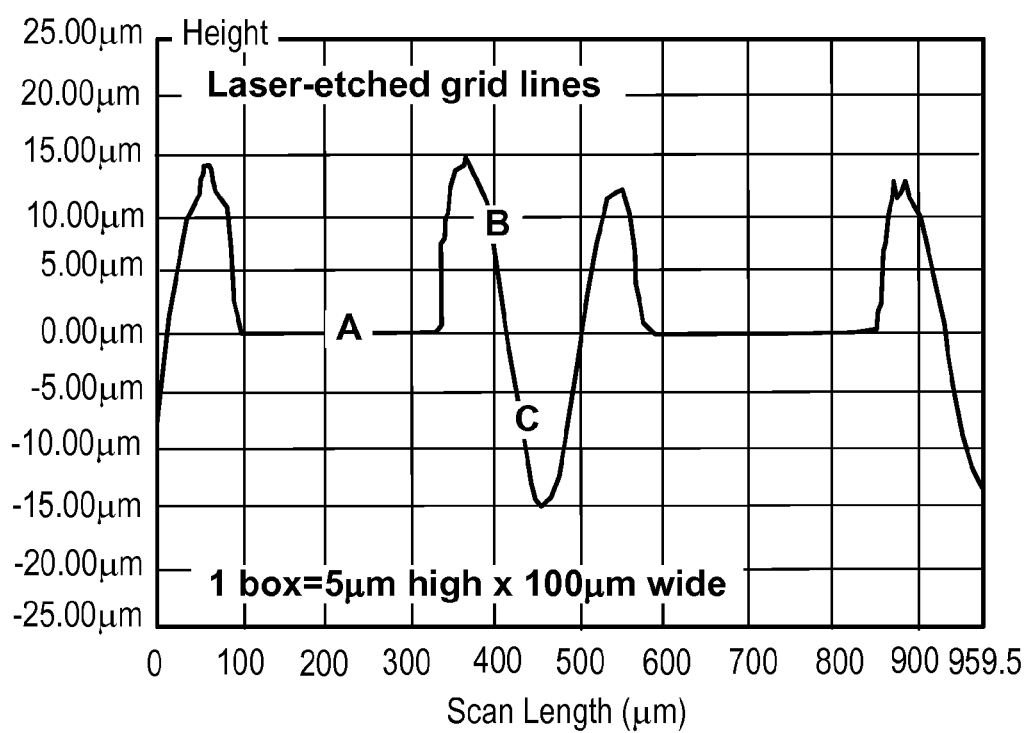

FIGS. 4A-4D show other embodiments, in which a regular pattern of gaps is formed by laser etching a pattern into release agent layer 210. In one example, a series of lines 400 is patterned into release agent layer 210, forming grooves 402, e.g., 15 μm deep, V-shaped grooves, between the lines (FIGS. 4A-4B). On either side of each groove 402 is a mound 404, e.g., approximately 10-15 μm in height, created by the settling of residue from the laser etching process and from a slight curvature of the release agent layer induced by laser etching. In another example, 0.5 μm spaced grid lines are laser etched into release agent layer 210, forming 250 μm by 250 μm islands 406 of release agent layer material separated by V-shaped grooves 408 (FIGS. 4C-4D). Mounds 410 form along the edges of islands 406.

FIG. 5 shows other embodiments, in which an irregular pattern of gaps is formed by mechanical abrasion (e.g., with sandpaper) of release agent layer 210. In the example shown, 400 grit sandpaper was used to roughen release agent layer 210, creating micro-scale divots in the release agent layer.

The percent area of backing 208 exposed to adhesive layer 204 (i.e., the areal fraction of release agent layer 210 occupied by gaps 300) controls the adhesion between adhesive layer 204 and support layer 206, as discussion in greater detail below. For laser etched lines in release agent layer 210, the percent area of exposed backing ($x_{lines}$) is calculated as the ratio of the width (w) of the lines to the spacing (W) of the lines. The length of the line equals the width of the backing, and thus cancels, leaving the following expression for $x_{lines}$:

$$x_{lines} = \frac{w}{W}$$

A similar expression can be developed for laser etched square grid lines. In particular, the percent area of exposed backing ($x_{grid\ lines}$) can be calculated for the smallest repeat unit in the pattern (i.e., a square) and then generalized via symmetry considerations. Each square has an exposed backing area of twice the width of the laser etched line multiplied by the center-to-center line spacing minus the overlapping portion of the lines at the corners of the squares, normalized by the area of the square repeat unit:

$$x_{grid\ lines} = \frac{2wW - w^2}{W^2}$$

Geometry of the micro-patterned release layer thus dictates the adhesion between adhesive layer 204 and support layer 206, enabling fine tuning of the mechanical properties of the quick-release tapes, as discussed in greater detail below.

In other embodiments, and as described in more detail below, the release agent layer is not patterned, but is made of one or materials that can be altered when it is time to remove the quick-release tape.

In some embodiments, the quick-release tape is incorporated into a device, such as a medical device. In these cases, the backing 208 may be attached to the device, e.g., by gluing or otherwise adhering the backing to the device. Alternatively, the backing 208 may be an integral part of the device.

Composition and Fabrication of the Quick-Release Tapes

Referring to FIG. 6, to fabricate quick-release tapes 200, a thin layer of release agent layer 210 is coated onto backing 208 (step 600), for instance, via gravure roll coating. In the examples described below, backing 208 is formed of 50 μm thick polyethylene terephthalate (PET); however, any suitable backing material having sufficient cohesive mechanical strength and appropriate biocompatibility characteristics can be used. For a quick-release tape with strong adhesion properties, backing 208 may be formed of a stiff material, such as polyethylene terephthalate, polyethylene, or paper. For a quick-release tape having adhesive flexibility and/or shock absorption properties, backing 208 may be formed of a flexible or extensible material, such as elastomers including, e.g., polydimethyl siloxane, polyurethanes, ethylene vinyl acetate, or butyl rubber. For instance, a flexible or extensible backing having shock absorption properties may be capable of, e.g., absorbing forces applied to a device fixed by the tape while preventing detachment of the device from the substrate, or preventing damage to the underlying substrate or adhesive tape, or improving comfort while the adhesive is fixed to tissue or during removal In some examples, for instance to achieve a quick-release tape that has both strong adhesion and flexibility, backing 208 may be formed of a combination of stiff and flexible materials. For instance, backing 208 may include a stiff material in a central region and a flexible material along the edges of the backing.

Release agent layer 210 is micro-patterned (step 602) to achieve a desired percent area of exposed backing, and hence a target adhesion between adhesive layer 204 and support layer 206. Micro-patterning the release layer opens gaps in the release layer to selectively expose portions of backing, such that when the adhesive layer 204 is positioned on the release layer, the viscous pressure sensitive adhesive flows into the gaps and contacts backing 208.

In one embodiment, laser etching is used to selectively etch the release agent layer material to form the desired pattern (for instance, the lines or grid lines in the images of FIGS. 4A-4D). Absorption of focused laser light during laser etching disrupts intermolecular bonds in the illuminated material, fracturing or vaporizing the material. Based on the depth of penetration of the light, which is a function of the absorption of the material at the wavelength of the laser, the inter-molecular bond strength, the power of the laser, the laser cutting speed, and the spot size, laser etching can be used either to etch a pattern into the release agent layer or to cut through the release agent layer and the backing, e.g., to separate a long strip into separate tapes, e.g., bandages.

In an alternative embodiment, the release agent layer is micro-patterned via mechanical abrasion, e.g., using sandpaper, to create micro-scale divots in the release agent layer. While micro-patterning via laser etching creates more regularly spaced features in the patterned release agent layer, mechanical abrasion is a more readily scalable process, and has the further advantage that it does not cause significant localized heating of the release agent layer or the backing.

The release agent layer may also be patterned via chemical etching, reactive ion etching, gravure roll coating, stamping, photo-thermal ablation, electron beam lithography, or another patterning method. The release agent layer may be patterned via a continuous process or a batch roll-to-roll process. In some instances, during patterning of the release agent layer, full thickness cuts are made through the backing to create porosity in the backing.

In some examples, the release agent layer may be formed of two different species that spinodally decompose or otherwise phase separate (e.g., a multi-component self-assembled monolayer). For example, two different polymers (referred to as polymer A and polymer B) may be dissolved in a common solvent or co-solvent system, or heated, and then cast into a film. Provided that polymers A and B phase separate during their transition from the liquid to solid phase, domains of one polymer (e.g., polymer A) will form in the other polymer (e.g., polymer B). If polymers A and B have different adhesion properties with respect to the adhesive layer, the relative surface area and arrangement of the two polymers affects the peel and shear adhesive properties. In some instances, more than two polymers can be used to tune the properties of the release agent layer. In other instances, polymers containing more than one monomer, such as diblock and triblock copolymers, can also phase separate on solidification. Examples of polymer blends that phase separate include, but are not limited to polyacrylic acid and polystyrene, polyethylene glycol and polystyrene, poly(glycidylmethacrylate) and polystyrene, and poly[1,6-bis(p-carboxyphenoxy)hexane] and poly(D,L-lactide-co-glycolide). Additionally, if added in sufficient quantity non-polymeric additives can also phase separate and produce domains in polymeric films.

The patterned release agent layer 210 is cleaned and adhesive layer 204 is applied onto release agent layer 210 (step 604). In one example, adhesive layer 204 is applied via solvent casting onto release agent layer 210 followed by solvent evaporation, which may be accelerated by heating. In another example, a transfer film of adhesive is formed separately, and the pre-formed, solvent evaporated transfer film is physically transferred onto release agent layer 210.

Adhesive layer 204 is formed of a pressure sensitive adhesive. In certain examples, adhesive layer 204 can be formed of an acrylic-based adhesive. However, any suitable adhesive having sufficient adhesion to the target substrate (e.g., skin) and, if required, appropriate biocompatibility characteristics, can be used. Release agent layer 210 is formed of a material having low adhesion or anti-adhesion to adhesive layer 204 and high adhesion to backing 208. Thus, for instance, a siloxane-based release agent may be used with an adhesive layer based on acrylic acid or on a hydrocolloid composition. A fluorosilicone-based release agent may be used with a silicone-based backing.

In some embodiments, quick-release tape 200 is produced by a roll-to-roll coating process, enabling the quick-release tape to be produced by readily scalable processes. For instance, an appropriate thickness of solvent-free or dissolved adhesives (e.g., acrylate or hydrocolloid- or silicone-based adhesives) are applied directly to the release agent layer coated backing. The adhesive is cured in place (e.g., by ultraviolet (UV) exposure or heat) or is thermally evaporated, yielding a pressure sensitive adhesive layer on the release agent layer coated backing. In some cases, if the backing or release agent layer is formed of a material that would be chemically or mechanically affected by the adhesive application and/or curing process, a transfer film is used to transfer already-cured adhesive onto the release agent layer coated backing. In this example, the adhesion between the transfer film and the adhesive layer is less than the adhesion between the adhesive layer and the release agent layer coated backing.

More generally, in some embodiments, the quick-release tapes described herein alter only the support layer/backing-adhesive interface; the skin-adhesive interface and the backing material remain unchanged as compared with standard medical tapes. Thus, the structure of the quick-release tapes is widely applicable to a variety of adhesives and backing materials, including, for instance, standard adhesives for which the skin irritability profiles have already been well characterized.

Alternative Compositions of the Quick-Release Tapes

In alternative embodiments, the release agent layer is a uniform layer that is environmentally sensitive and degrades when in the presence of a cue. The degradation of the release agent layer allows for easy removal of the backing from the adhesive layer.

For instance, an enzyme-degradable release agent layer is formed of co-polymers synthesized from low molecular weight, biocompatible, non-degradable pre-polymers and peptides or oligosaccharides connected by enzyme-labile linkers. Such a release agent layer may be applied using a variety of methods, such as roll coating, spin coating, evaporation, or other deposition methods. Exemplary pre-polymers include, for instance, polyethylene glycol, polyurethanes, matrix metalloproteinase sensitive hydrogels, esterase sensitive materials (including cross-linked, uncross-linked, and self-assembled gels), and cellulose derivatives.

When an enzyme solution (e.g., a peptidase or amylase solution) is applied, e.g., as a liquid or via an applicator, such as a cotton swab, the peptide bonds or glycosidic bonds in the release agent layer are broken, yielding low molecular weight constituents with little mechanical strength. In some cases, peptidases can be applied to cleave peptide sequences that have been introduced into the polymer backbone. For instance, chymotrypsin may be used to cleave tyrosine-tyrosine linkages. In these embodiments, peptide sequences are covalently attached within thermoplastic polymers as cleavage sites. In the presence of the enzyme (i.e., the peptidase), the peptide bonds are broken. As a result, the average molecular weight of the polymer chains is reduced, weakening the mechanical linkage between the backing and adhesive layers provided by the polymer layer. In some cases, the polymer forming the release agent layer is a solid; upon addition of the enzyme, the polymer release agent layer is liquefied. Increasing the enzyme concentration, among other factors, can increase the speed of the degradation.

In another example, the release agent layer is a pH sensitive layer. A pH sensitive layer can be fabricated, for instance, via layer-by-layer deposition of oppositely charged macromolecules; or by coating the backing with a pH-sensitive thermoplastic polymer. For instance, the pH sensitive release agent layer may be formed from pH sensitive polyacrylate or gelatin derivatives. In these examples, when the release agent layer is wet with de-ionized water (e.g., as may occur during washing or long-term placement in an incubator environment), the release agent layer remains intact. A change in pH, such as a change of 0.25, 0.5, or 1, causes the release agent layer to dissolve. In some cases, the pH sensitive layer includes a polyanion and a polycation that are water insoluble and dissolves in an ionic solution.

In an alternate example, the release agent layer is photodegradable. For instance, the release agent layer is formed of a polymer that rapidly degrades into low molecular weight components when exposed to light of a particular wavelength. Photodegradable monomers include but are not limited to, for example, tert-butyl-4-vinylphenyl carbonate. The degraded release agent layer loses mechanical strength, allowing the support layer to be easily removed.

In some examples, the release agent layer swells, reducing its mechanical integrity and thus the force sufficient for removal of the support layer, in the presence of certain solvents or other materials. For instance, the release agent layer may be formed of a material that swells in the presence of saline or isopropanol, such as, for instance, cellulose derivatives, polyurethanes and hydrogels.

In another example, either the release agent layer or the backing is formed of a shape memory material made up of fibrillar structures. When a shape memory polymer is exposed to a temperature above its transition temperature, it reverts to its "locked-in" shape. In doing so, the fibrillar structures in the material change from adhesive to non-adhesive, which would facilitate removal of the support layer of the quick-release tape. An exemplary shape memory material is described in "A Path to Strong and Reversible Dry Adhesives" (Advanced Materials, 22:2125-2137, 2010), the contents of which are incorporated herein by reference.

In some examples, release agent layer 210 can include a release modifying agent such that the release agent layer 210 is anti-adhesive to certain types of adhesives, such as acrylic adhesives. For instance, release agent layer 210 can be formed of a silicone-based material or a fluorosilicone-based material and modified with a resin, such as a siloxane resin. Examples of these materials can be found, for example, in U.S. Pat. No. 5,696,211 and in PCT Publication No. WO2012128919, the entire contents of both of which are incorporated herein by reference.

In another alternative embodiment, the support layer includes only a single layer. For instance, the support layer is formed of a polymer that has poor interfacial or normal adhesion (e.g., the adhesion in a direction perpendicular to the interface) with the adhesive layer. One potential materials combination is a silicone support layer with an acrylate adhesive; and alternative combination is a fluorosilicone support layer with a silicone-based adhesive.

Another example of a single-layer support layer is a support layer formed of a directional adhesive. For instance, the support layer may be formed of a uni-directionally stretchable fabric embedded in silicone. When shear is applied perpendicular to the stretch axis in the inextensible direction of the fabric, the layer adheres strongly to the adhesion layer. When the fabric is stretched along the elastic axis, the layer releases with little force. An exemplary directional adhesive is described in "Looking Beyond Fibrillar Features to Scale Gecko-Like Adhesion" (Advanced Materials, 24(8)1078-83, 2012), the contents of which are incorporated herein by reference.

In another embodiment, micro- or nano-patterning of the support layer, rather than a release agent layer, can be used to create a directionally anisotropic adhesive. For instance, micro-scale pillars with angled features have demonstrated directionally dependent adhesion. Such pillars would enable strong shear adhesion (e.g., adhesion in the plane of the interface) between the support layer and the adhesive layer, but would allow the support layer to be peeled with low force. Exemplary descriptions of the structure and fabrication of such pillars can be found in "Directional adhesion of gecko-inspired angled microfiber arrays" (Applied Physics Letters, 93:191910-12, 2008) and "A nontransferring dry adhesive with hierarchical polymer nanohairs" (PNAS, 106 (14)5639-5644, 2009), the contents of both of which are incorporated herein by reference.

Mechanical Properties of the Quick-Release Tapes

The quick-release tapes described herein are quickly and easily removable from a substrate without inflicting damage to the substrate. To achieve such removal, the adhesion between the adhesive layer and the support layer is tuned to be less than the adhesion between the adhesive layer and the substrate. As a result, when the quick-release tapes are peeled from the substrate (e.g., by applying a normal force perpendicular to the interface between the tape and the substrate), the support layer is peeled away from the adhesive layer, leaving the adhesive layer on the substrate while imparting minimal force on the substrate. That is, by designing the quick-release tapes to fail at an internal interface (i.e., between the adhesive layer and the support layer), the stress and strain experienced by the substrate can be minimized, reducing the potential for damage to the substrate.

Referring again to FIG. 3, the micro-patterned release agent layer includes regions of high adhesion and regions of low adhesion or anti-adhesion between the support layer and the adhesive layer. Within gaps 300, the adhesive layer 204 contacts and adheres to backing 208; that is, the adhesion between the adhesive layer and the support layer is high in gaps 300. Where release agent layer 210 is present, the release agent layer contacts adhesive layer 204; these regions have low adhesion or anti-adhesion.

The overall adhesion between adhesive layer 204 and support layer 206 is tuned by the relative fraction of highly adhesive regions to lower, non-, or anti-adhesive regions. That is, the adhesion between adhesive layer 204 and support layer 206 can be tuned by varying the percent area of exposed backing (e.g., $x_{lines}$ or $x_{grid\ lines}$, in the case of a laser etched release agent layer). To ensure that support layer 206 can be removed without removing adhesive layer 204 from substrate 202, the adhesion between adhesive layer 204 and support layer 206 is controlled via the geometry of the micro-patterned release agent layer 210 to be less than the adhesion between adhesive layer 204 and substrate 202.

The adhesion between adhesive layer 204 and support layer 206 can be adjusted as high as a standard medical tape having the given combination of adhesive and backing materials by causing 100% of backing 208 to be exposed to adhesive layer 204 (i.e., by removing all of release agent layer 210). Similarly, the adhesion between adhesive layer 204 and support layer 206 can be adjusted as low as an extremely weak adhesive by allowing none of backing 208 to be exposed to adhesive layer 204 (i.e., by removing none of release agent layer 210). That is, by varying the percent area of exposed backing, the adhesion of adhesive layer 204 to support layer 206 can tuned to any value between the upper bound of the adhesion of the pure polymer backing to adhesive layer 204 and the lower bound of adhesion of the fully release agent layer coated backing to adhesive layer 204.

In addition to achieving low adhesion at the interface between adhesive layer 204 and support layer 206, quick-release tape 200 exhibits high shear strength at both the interface between adhesive layer 204 and substrate 202 and the interface between adhesive layer 204 and support layer 206. Furthermore, with the choice of a sufficiently strong adhesive, a high normal adhesion between adhesive layer 204 and substrate 202 can be achieved. High shear strength and normal adhesion to substrate 202 help to maintain device fixation, for instance, during motion of skin relative to the adhesive layer of the tape.

When quick-release tape 200 is peeled from substrate 202, the geometry of release agent layer 210 and the interfacial chemistry and rheology of adhesive layer 204 govern crack propagation. At each juncture of backing 208, release agent layer 210, and adhesive layer 204 (e.g., a juncture 302), a propagating crack can either continue to propagate along the support layer-adhesive layer interface, leaving residual adhesive on the substrate; or along the adhesive layer-substrate interface, pulling the adhesive off of the substrate. By closely spacing laser etched lines in release agent layer 210, crack propagation can be forced along the support layer-adhesive layer interface, thus causing residual adhesive to remain on the substrate.

As shown in FIG. 7A, residual adhesive 204 can be removed from substrate 202 by pushing and rolling the adhesive, possibly because a sufficient thickness of adhesive has been left on the surface. However, pushing and rolling the adhesive is often not suitable for fragile skin. In some cases, leaving residual adhesive on the skin may be safer than removal of the adhesive. If left tacky, however, the residual adhesive could potentially adhere to other surfaces (e.g., clothing or bedding), again introducing the possibility of skin damage.

As shown in FIG. 7B, a powder, such as talcum powder, can be applied to residual adhesive 204. Once fouled with a layer of powder (depicted as a layer 700), residual adhesive 204 no longer exhibits tack. Furthermore, the powder-fouled residual adhesive 700 does not recover its tackiness when exposed to water, which is an important characteristic of a tape that is to be used in a humid neonatal incubator environment or, more generally, in a medical setting in which washing with water occurs.

In medical settings, the ability to affix, remove, and re-affix or reposition devices with adhesives is important. A second medical tape can be applied over the washed, powder-fouled residual adhesive 700; the second tape adheres to the powder-fouled residual adhesive 700 with substantially the same force with which it would have adhered to the substrate directly. That is, the washed, powder-fouled residual adhesive serves as a suitable attachment site if reattachment of a new tape is necessary before the residual adhesive has sloughed off or otherwise been removed.

Applications and Uses of the Quick-Release Tapes

FIGS. 8A-8C show an example of quick-release tape 200 used to affix an endotracheal (ET) tube 800 to skin 802. Intact quick-release tape 200 strongly secures tube 800 to the skin due to the mechanical cohesion provided by the backing (FIG. 8A), the shear strength of the intratape interfaces, and the normal adhesion of the adhesive layer to skin 802. Once support layer 206 is removed (FIG. 7B), the cohesive strength of the residual adhesive 204 determines the degree of device fixation. Because adhesives do not generally have a high cohesive strength, tube 800 can easily be removed (FIG. 8C), leaving a gap 804 in residual adhesive 204.

Figure 9:
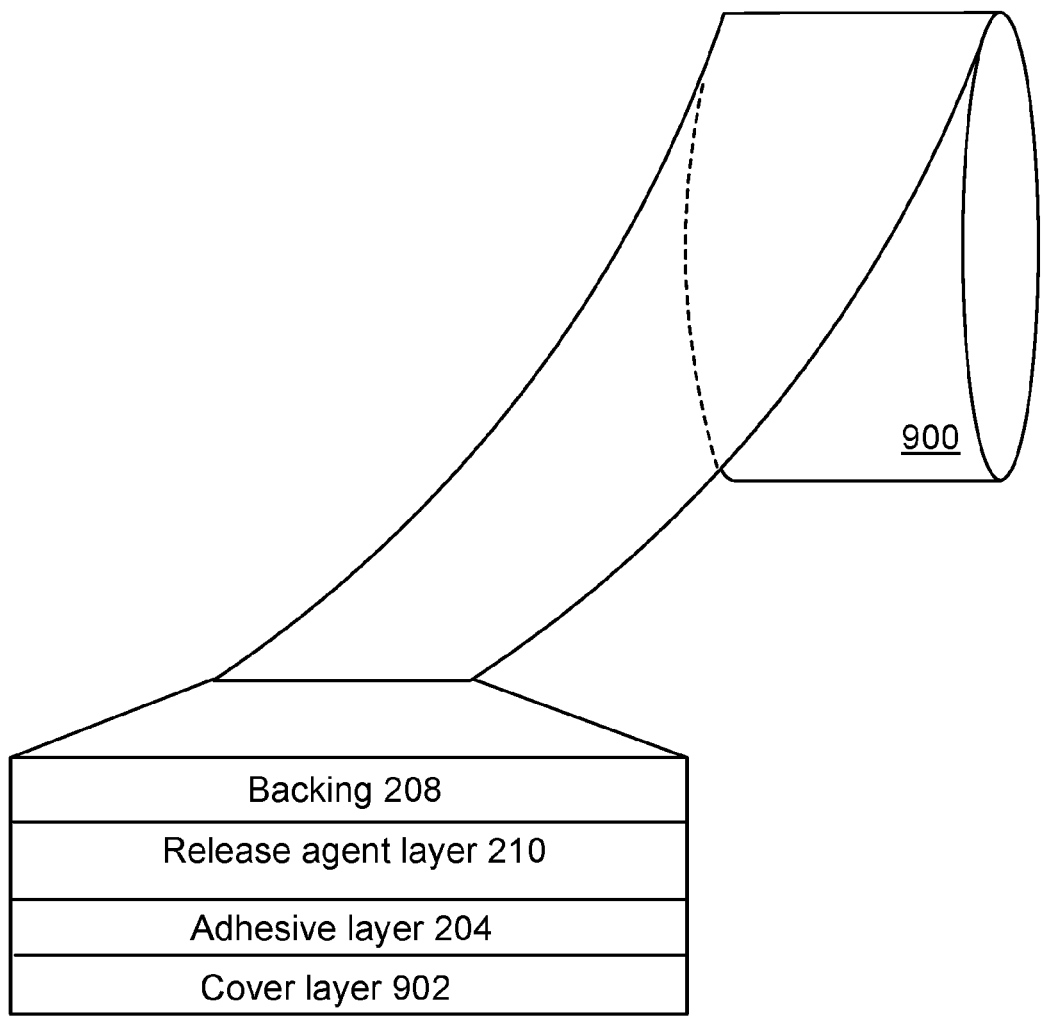
FIG. 9 is a schematic diagram of a roll of quick-release tape.

Referring to FIG. 9, quick-release tapes can be provided in a roll 900. To ensure that adhesive layer 204 does not stick to the back side of backing 208 when the tape is formed into a roll, an anti-adhesive cover layer 902 is placed on the side of adhesive layer 204 opposite release agent layer 210 such that when rolled up, cover layer 902 contacts backing 208. Cover layer 902 is designed and selected such that the adhesion between adhesive layer 204 and support layer 206 is greater than the adhesion between adhesive layer 204 and cover layer 902. For instance, cover layer 902 may be formed of the same material as release agent layer 210, but with no pattern, thus preventing any of the back side of backing 208 from being exposed to adhesive layer 204 and ensuring a low adhesion between adhesive layer 204 and the back side of backing 208.

Figure 10A:
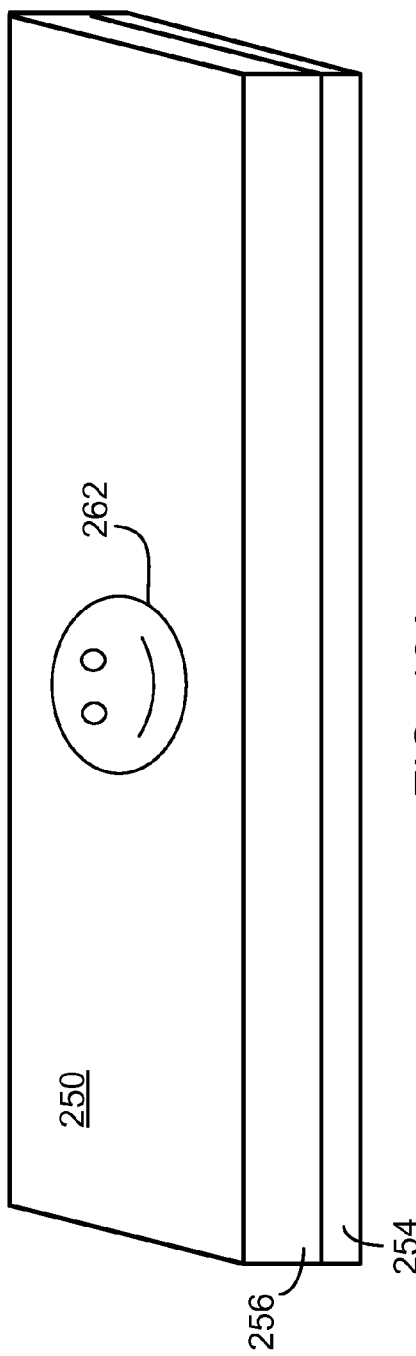
FIGS. 10A-10B are schematic diagrams of a quick-release tape including multiple images.
Figure 10B:
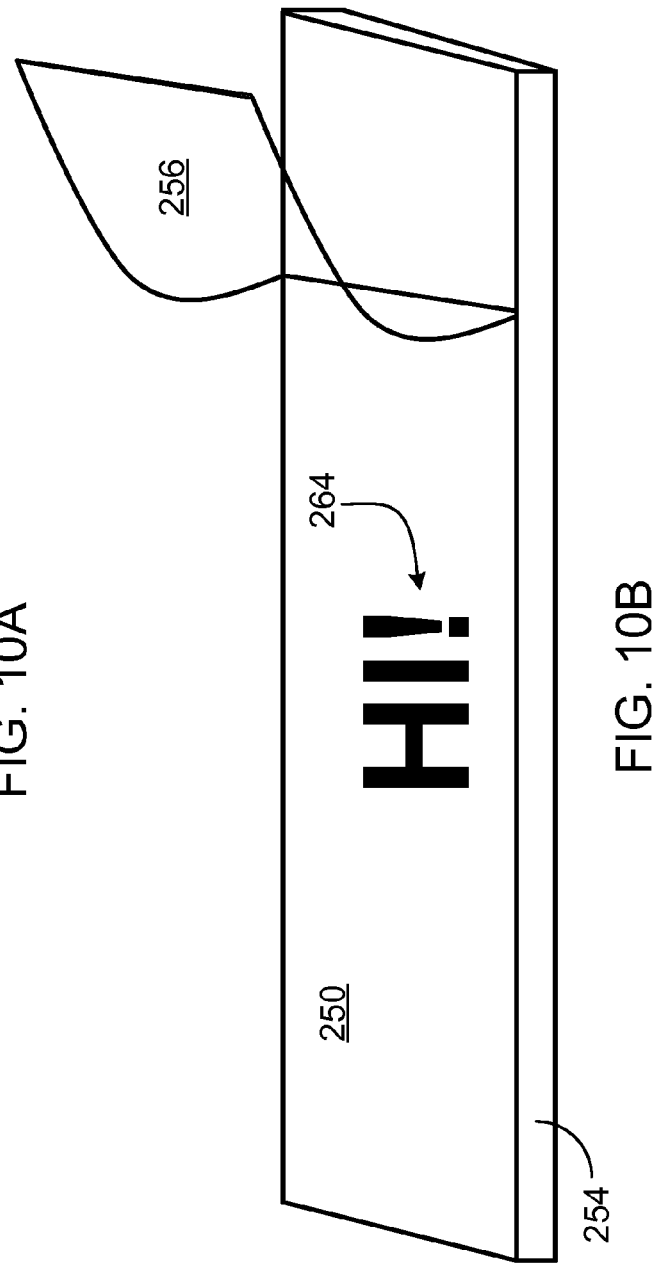

Referring to FIGS. 10A and 10B, a quick-release tape 250 includes an adhesive layer 254 and a support layer 256. A first image 262 is displayed on the support layer 256 (FIG. 22A), such that when the quick-release tape 250 is first applied to a substrate (e.g., as a medical bandage), the first image 262 is shown. When support layer 256 is removed (FIG. 22B), a second image 264 displayed on adhesive layer 254 is shown. The images 262 and 264 are not limited to the images depicted in the Figures, but may be any letters, symbols, designs, or other images, and may include a single color or multiple colors.

The structure of the quick-release tapes described herein is not limited to use with a tape, but can apply equally to any medical adhesive, including, e.g., bandages, adhesive electrodes, adhesive temperature probes, and adhesive medical devices.

EXAMPLES

The invention is further described in the following examples, which do not limit the scope of the invention described in the claims.

The following examples generally show comparative strengths of various types of tapes, demonstrating that the quick-release tapes described herein have a peel strength lower than that of conventional tapes. The examples further demonstrate that the morphology of the release agent layer of the quick-release tapes described herein affects the adhesion of the tape. The use of such quick-release tapes in affixing an endotracheal (ET) tube to a substrate is also demonstrated. In addition, the implications of leaving residual adhesive on the substrate after tape removal are explored.

Peel force, probe tack, and device removal force may change as a function of removal speed. In the specific examples described below, peel tests were performed at a removal rate of 5 mm/s as specified by the Pressure Sensitive Tape Council (PSTC). Probe tack tests were performed such that a 1 cm diameter flat, aluminum probe contacted the adhesive layer at a target force of approximately 3 N for 30 seconds and was then withdrawn at a rate of 1 mm/s. As exemplary devices affixed by quick-release tape, uncuffed neonatal endotracheal tubes were pulled from the surface at a rate of 5 mm/s. However, alternative testing methodologies exist and may also be applied to test the properties of the quick-release tape described herein.

Example 1—Preparing a Multi-Layer Quick-Release Tape

A quick-release tape was formed by coating a siloxane-based release agent (Dow Corning Syl-Off® SL 9106 Coating, Auburn, Mich.) onto a 50 μm thick PET backing sheet using a Euclid Coating Systems Single Roll Coater (Bay City, Mich.). To cure the two-part release agent, the coated backing sheets were placed in a drying oven for 5 minutes at 180° C.

To micro-pattern the release agent layer, a pattern was drawn using CorelDRAW® Graphics Suite X5 (Mountain View, Calif.). The pattern was etched into the release agent layer using a 30 Watt VersaLASER® VLS 2.3 (Universal® Laser Systems, Scottsdale, Ariz.) with the laser cutting speed set to 100%, the power set to 10%, and the pulses per inch (PPI) set to 1,000 to make partial thickness cuts that extended about 20 µm into the backing. The patterned sheets were then cut into strips of tape using the VersaLaser® with the power set to 50% and the other settings maintained as above. The strips were cleaned in 70% ethanol to remove residual particles.

Figure 11A:
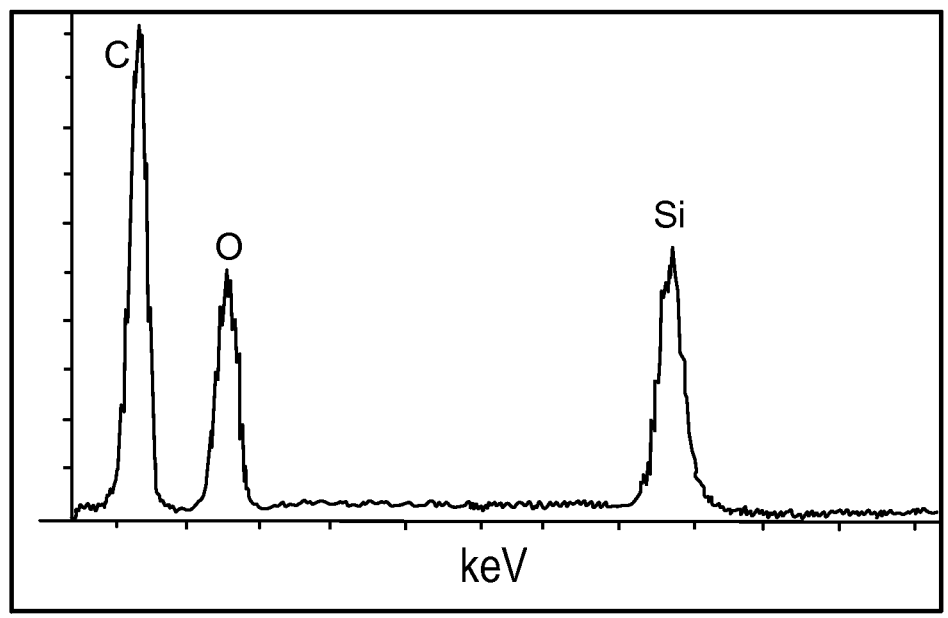
FIGS. 11A-11B are elemental analyses of the grid patterned release agent layer of FIG. 4B performed by energy-dispersive spectroscopy analysis.
Figure 11B:
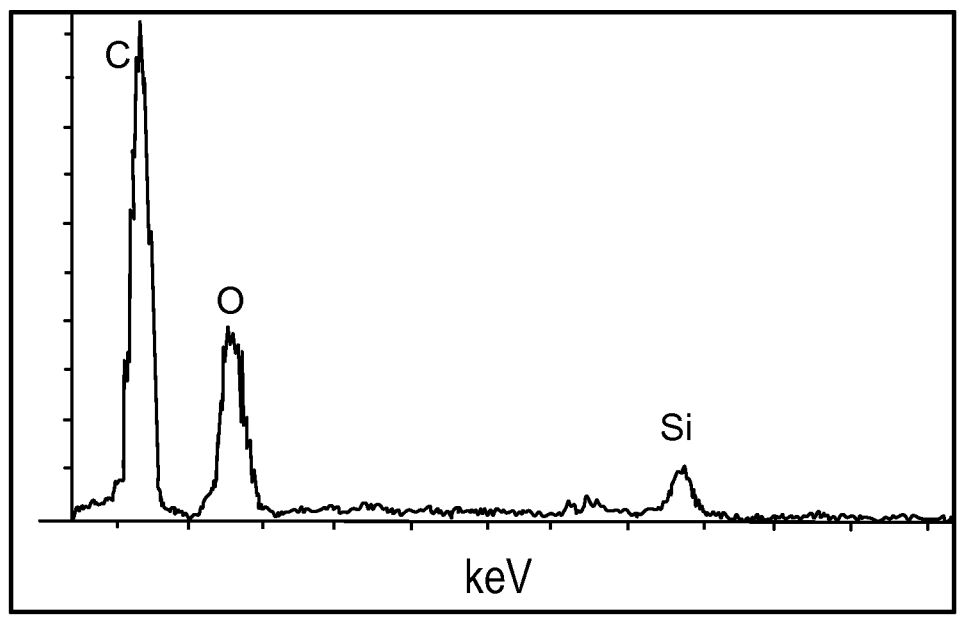

Referring to FIGS. 11A-11B, after release agent layer micro-patterning, elemental analysis was performed by energy-dispersive spectroscopy analysis to confirm the removal of release agent in the desired regions using a Zeiss Ultra 55 field emission scanning electron microscope (Carl Zeiss AG, Oberkochen, Germany) equipped with energy-dispersive spectroscopic elemental analysis. Carbon, oxygen, and silicon levels were quantified within laser etched lines and between the lines. The release agent layer coated region (FIG. 11A) shows higher silicon content relative to carbon and oxygen than the etched lines (FIG. 11B), indicating that the siloxane-based release agent layer is intact. The etched lines, in contrast, display low silicon content, indicative of a PET surface (i.e., the backing) with negligible residual siloxane release agent.

Surface profilometry analysis of the patterned release agent layer, for instance as shown in FIGS. 4A-4D and FIG. 5, was performed using a Tencor P-10 Surface Profilometer (KLA-Tencor, Milpitas, Calif.) equipped with a 2 µm radius diamond tipped stylus.

An adhesive layer was applied to the patterned release agent layer by solvent casting pressure sensitive adhesive (GELVA® GMS 2999, Cytec Industries Inc., West Paterson, N.J.) and heating at 60° C. to accelerate solvent evaporation. In alternative embodiments, a transfer film of adhesive can be formed (Syntac Coated Products, New Hartford, Conn.) and physically transferred onto the patterned release agent layer.

Example 2—Tape Removal from a Paper Substrate

Figure 12A:
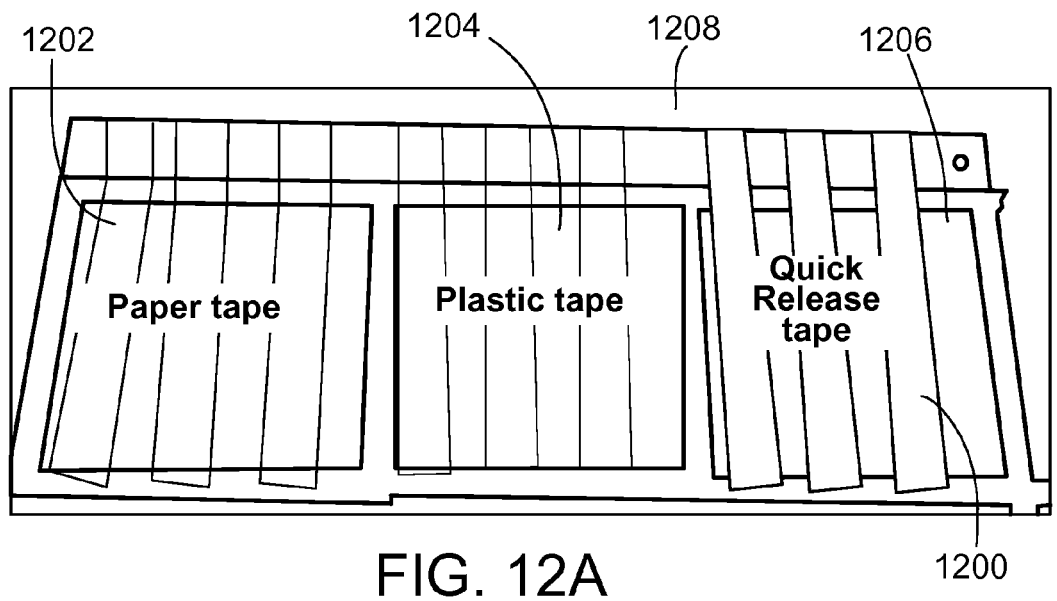
FIGS. 12A and 12B are photographs of the experimental setup and results, respectively, of a peel test of tapes from a paper substrate.
Figure 12B:
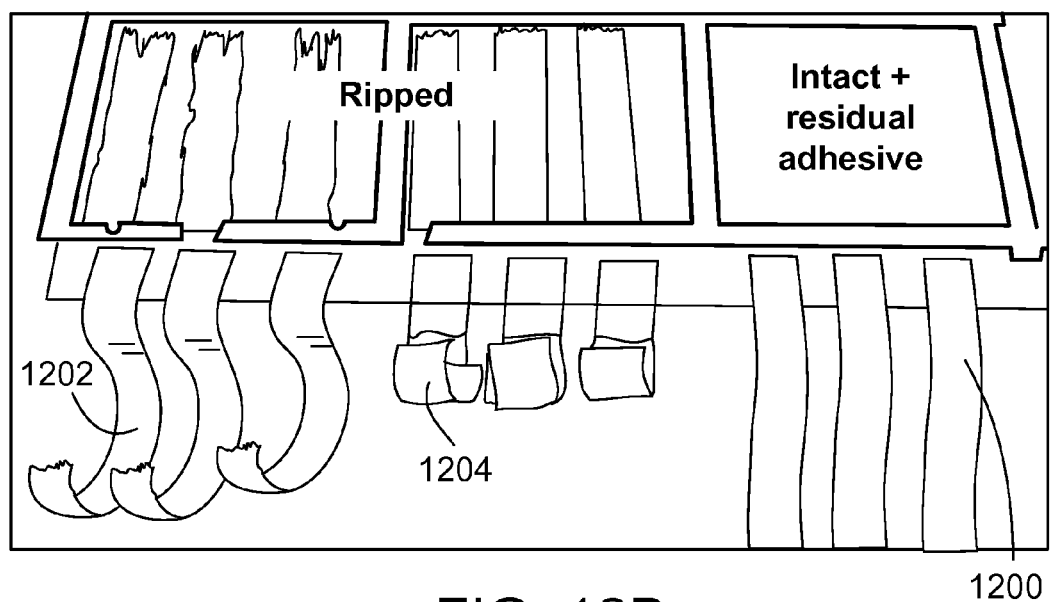

Referring to FIGS. 12A-12B, to experimentally illustrate the concept of damage free removal of the quick-release tape, strips of quick-release tape 1200, conventional paper-backed medical tape 1202 (3M™ Micropore™ Medical Tape), and conventional plastic-backed medical tape 1204 (3M™ Transpore™ Medical Tape) were affixed to colored origami paper 1206 taped to a laboratory bench 1208. To ensure even fixation, the tapes were applied using a 10 pound hand roller (ChemInstruments, Fairfield, Ohio). One end of each strip of tape was wrapped around a metal ruler. To simulate an emergency response scenario, the metal ruler was rapidly pulled (about 5 cm/s), peeling all of the tape strips from the paper.

The conventional tapes 1204 and 1206 rip the colored portion of the origami paper, exposing the underlying white paper. Quick-release tape 1200 does not damage the origami paper, and leaves behind residual adhesive on the surface of the paper.

Origami paper can be considered a proxy for sensitive neonatal skin given that it is easily damaged during rapid removal of conventional tape. In particular, under the conditions of the test, removal of conventional tapes causes tearing of the superficial layer (the colored portion of the origami paper) from the deep layer (the underlying white paper), akin to stripping of skin by removal of medical tape. Given that the quick-release tape does not induce tearing when removed from the origami paper under the same conditions, it can be inferred that the quick-release tape transmits significantly less force to the underlying substrate than do conventional tapes.

Example 3—Tape Removal from a Stainless Steel Substrate

Ninety degree peel tests were conducted under conditions prescribed by the Pressure Sensitive Tape Council (PSTC) to determine the average and maximum peel forces of various types of tape from a stainless steel surface. A two-layer tape formed of poly(ethylene terephthalate) (PET) backing with a solvent cast strong acrylic adhesive was tested to determine the strength of the acrylic adhesive that is used in the exemplary quick-release tapes tested in other examples described herein. Note that this tape, referred to as "PET tape," does not include a release agent layer. The PET tape was compared to commercially available plastic- and paper-backed medical tapes (3M™ Transpore™ Medical Tape and 3M™ Micropore™ Medical Tape, respectively). In addition, a tape with a weak adhesive designed for gentle removal from neonates (NeoFlex™ tape for use in neonatal environments, NeoTech) was tested.

Figure 13B:
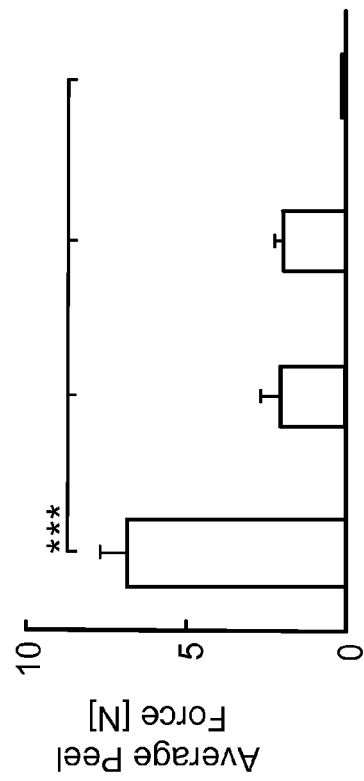
FIGS. 13B and 13C are plots of the average peel force and maximum peel force, respectively, for the stainless steel peel test of FIG. 13A.
Figure 13C:
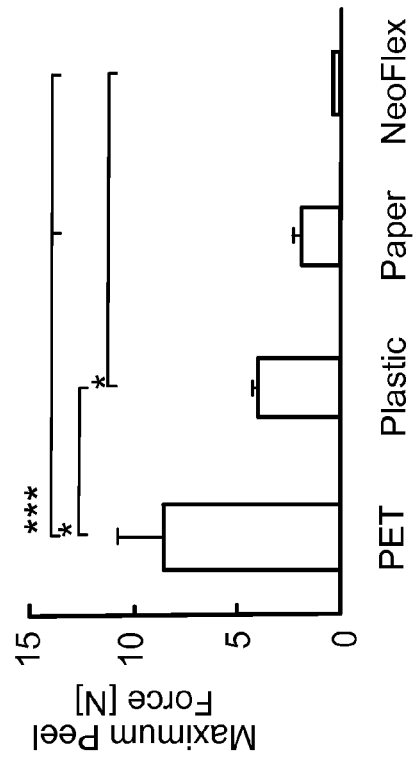
Figure 13A:
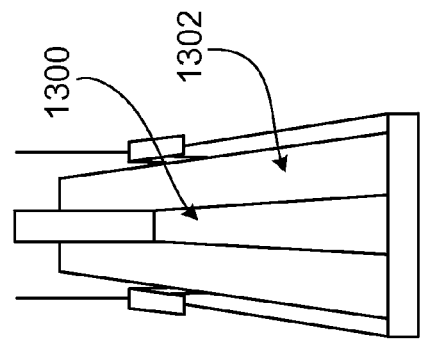
FIG. 13A is a schematic diagram of an experimental setup for a 90 degree peel test of various types of tapes from a stainless steel substrate.
Figure 14B:
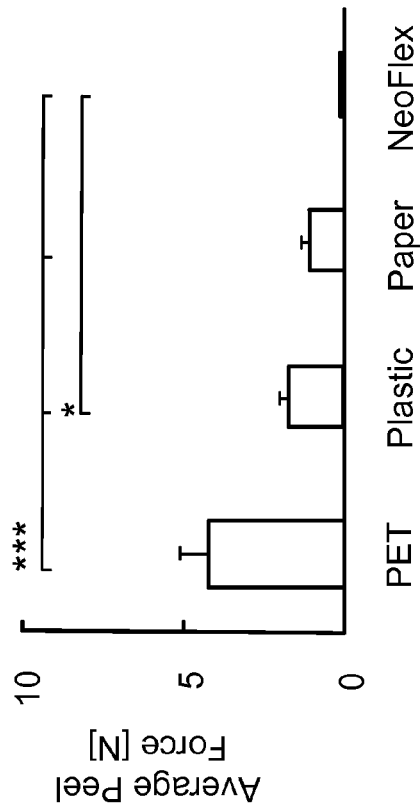
FIGS. 14B and 14C are plots of the average peel force and maximum peel force, respectively, for the forearm peel test of FIG. 14A.
Figure 14C:
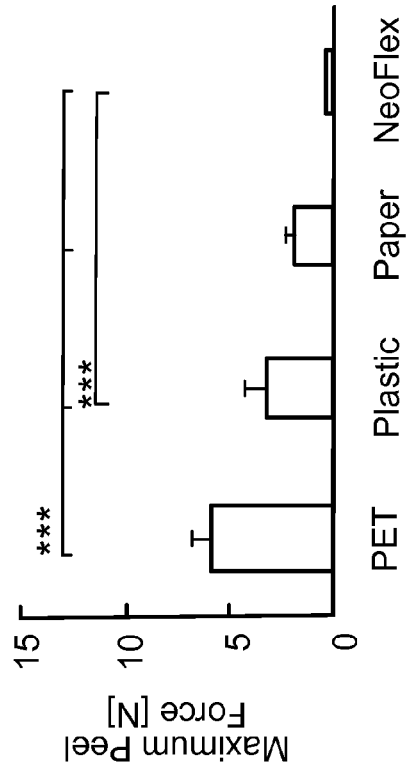
Figure 14A:
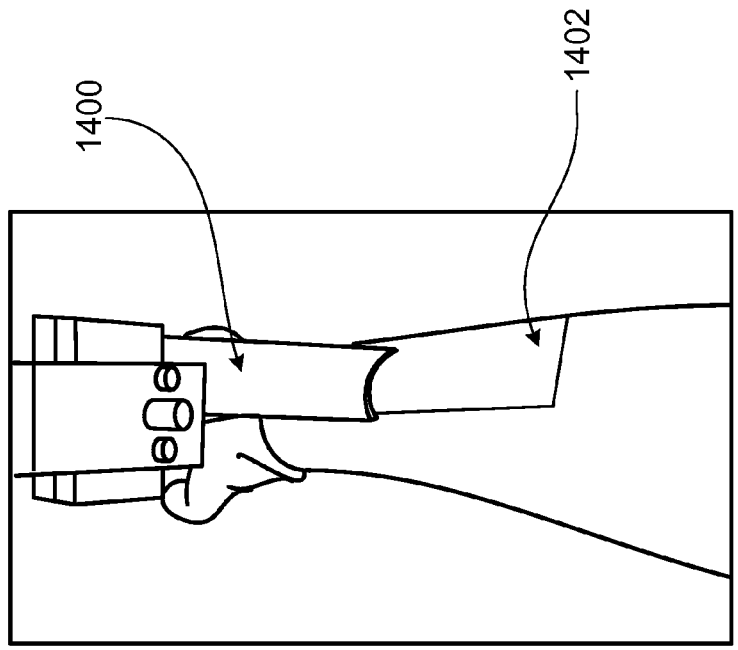
FIG. 14A is a photograph of an experimental setup for a 90 degree peel test of tape from medial ventral forearm skin.

Referring to FIG. 13A, to conduct the tests, a strip of tape 1300 was adhered to a polished 304 stainless steel plate 1202. The tape was peeled from the stainless steel plate at a 90 degree angle at a rate of 5 mm/s using an ADMET eXpert 7600 single column mechanical tester equipped with a 90 degree peel testing fixture (Norwood, Mass.). For each tape, the average peel force and the maximum peel force were determined. The average peel force was calculated by averaging peel force data (N=3) acquired at a peel distance of 5-10 cm. The maximum peel force was determined by identifying the maximum force reached during the peel test.

Referring to FIGS. 13B and 13C, the average and maximum peel forces for the PET tape are more than twice the peel forces of commercially available plastic- and paper-backed tapes, and more than an order of magnitude greater than the peel forces of NeoFlex™.

These results demonstrate that the adhesive that is used for the exemplary quick-release tapes tested in the examples that follow is a strong adhesive. High adhesive strength is not required for all neonatal medical tape functions, nor, more generally, is it necessary for the quick-release tapes described herein. However, the examples in this disclosure utilize a strong adhesive to emphasize that rapid, damage-free removal of the quick-release tapes can be achieved without sacrificing adhesive strength.

In Example 3 (and in all subsequent examples), data were compared by one-way analysis of variance (ANOVA) with post hoc Tukey's Honestly Significant Difference in means with the Bonferroni correction applied as appropriate (AnalystSoft, Alexandria, Va.). All plots show N=3; error bars indicate the mean plus one standard deviation; the results have p-values as follows: *$p<0.05$, $p<0.01$, *$p<0.001$.

Example 4—Tape Removal from Skin

Referring to FIGS. 14A-14C, 90 degree peel tests were conducted for tape 1400 peeled from medial ventral forearm skin 1402. The conditions of the peel tests and the tapes tested are as described in Example 3.

The trends in peel force from forearm skin match the trends observed in the stainless steel peel tests of Example 3. However, the average and maximum peel forces for each type of tape are lower from forearm skin than from stainless steel, which is consistent with the known performance of pressure-sensitive adhesives on skin versus stainless steel.

Example 5—Effect of Macro-Scale Surface Area of Backing-Adhesive Interaction

Peel tests were conducted to determine the effect of varying, on the macro-scale, the percent area of exposed backing on the adhesion of the quick-release tapes.

Figure 15B:
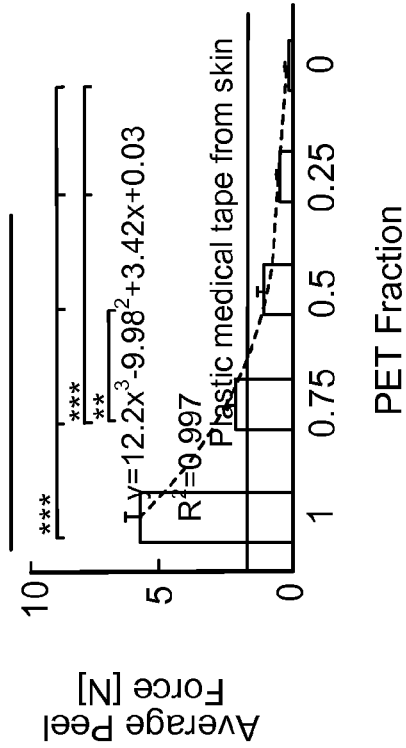
FIGS. 15B and 15C are plots of the average peel force and maximum peel force, respectively, for the peel test of FIG. 15A.
Figure 15C:
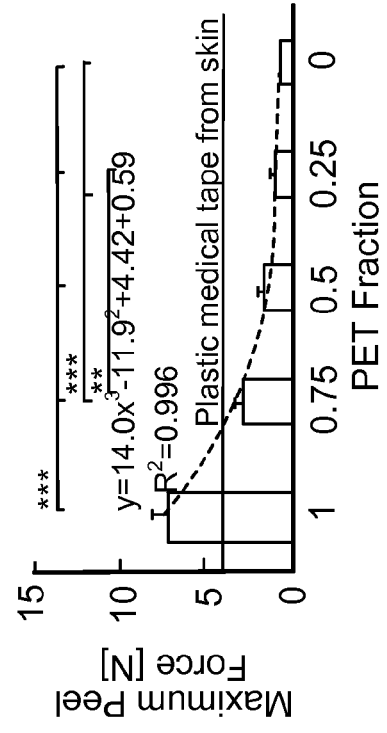
Figure 15A:
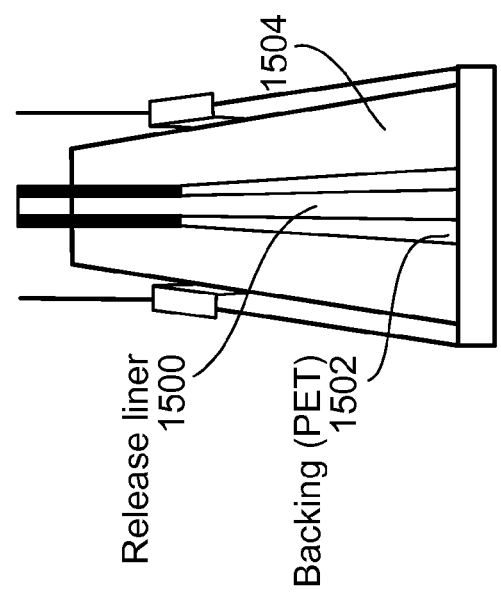
FIG. 15A is a schematic diagram of an experimental setup for a 90 degree peel test from a substrate coated with an acrylic-based adhesive.

Referring to FIG. 15A, strips of release agent coated PET 1500 were laser cut to widths of 25%, 50%, 75%, and 100% of the width of a 25 mm wide PET backing. Each laser cut strip was placed in the center of a PET backing 1502 and affixed to the backing using a 10 pound hand roller. An acrylic-based adhesive layer was applied as described above to form a macro-scale patterned quick-release tape. The tapes were peeled at 90 degrees from a polished stainless steel plate 1504 while monitoring force as a function of peel distance. The average and maximum peel forces were determined as a function of the percentage of exposed PET (i.e., the PET fraction as opposed to the release agent fraction).

Referring to FIGS. 15B and 15C, 100% PET (i.e., a backing with no release agent layer) showed strong adhesion to the adhesive layer, while a release agent coated PET (0% PET) exhibited negligible adhesion to the adhesive layer.

Both average and maximum peel forces exhibited an inverse cubic function dependence of peel force on the surface area of interaction between PET and the adhesive layer. Without wishing to be bound by theory, these results suggest that van der Waals forces, as predicted by the Derjaguin approximation ($F \sim 1/D^3$) dominate the interaction between the adhesive layer and the release coated backing, rather than chemical bonding or polymer chain interpenetration.

Example 6—Effect of Laser Etched Release Agent Layer on Adhesion

Peel tests were conducted for quick-release tapes having release agent layers micro-patterned via laser etching to determine the effect of line spacing on adhesion. Release agent layers coated onto strips of PET backing were patterned using laser etching as described above to form 100 μm wide lines spaced (center-to-center) by 0.5 mm, 1 mm, 2 mm, 4 mm, and 8 mm. An acrylic acid-based adhesive was solvent cast onto each patterned release agent layer to form a tape strip. The tape strips were adhered to a stainless steel substrate and a 90 degree peel test was conducted as described above to measure the average and maximum peel force for each tape.

Figure 16A:
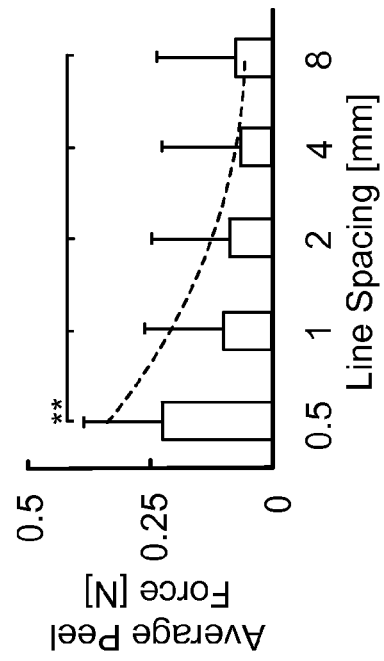
FIGS. 16A and 16B are plots of the average peel force and maximum peel force, respectively, as a function of the spacing of laser-etched lines in the release agent layer of a quick-release tape.
Figure 16B:
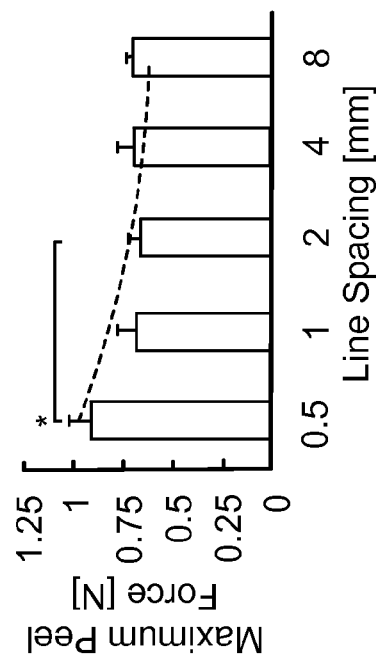

Referring to FIGS. 16A-16B, lines spaced by 0.5 mm provide a modest increase in average and maximum peel force over more widely spaced lines and over PET coated with unpatterned release agent layer (shown in FIGS. 15B-15C).

Theoretical peel forces were calculated as a function of the percent area of exposed backing ($x_{lines}$) according to the inverse cubic function, as suggested by the curve fit for the macro-scale experiment described in Example 5. The experimental average and maximum peel forces for the micro-patterned tape strips are in good agreement with the theoretical peel forces (shown as a dashed line), confirming the prediction that the percent area of exposed backing dictates the adhesion between the support layer and the adhesive layer.

Peel tests were also conducted for quick-release tapes having release agent layers micro-patterned with grid lines to determine the effect of grid line spacing on adhesion. Release agent layers coated on strips of PET backing were laser etched to form 100 μm wide grid lines spaced (center-to-center) 0.5 mm, 1 mm, 2 mm, 4 mm, and 8 mm. An acrylic acid adhesive layer was solvent cast onto each patterned release agent layer to form a tape strip. The tape strips were adhered to a stainless steel substrate and a 90 degree peel test was conducted as described above to measure the average and maximum peel force for each tape.

Figure 17A:
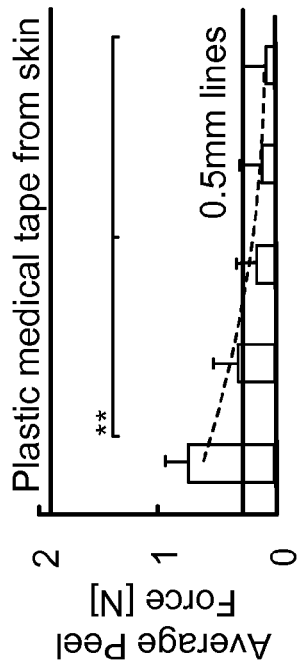
FIGS. 17A and 17B are plots of the average peel force and maximum peel force, respectively, as a function of the spacing of laser-etched grid lines in the release agent layer of a quick-release tape.
Figure 17B:
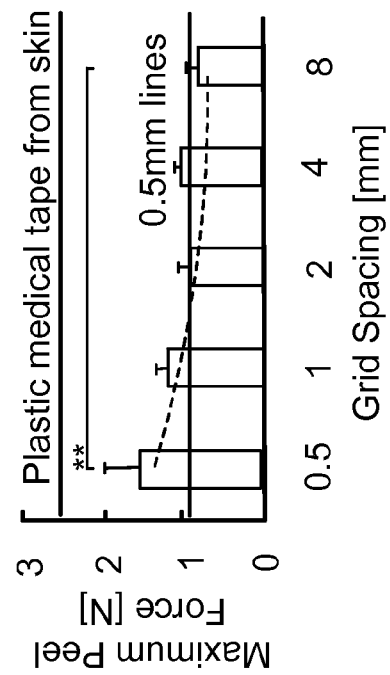

Referring to FIGS. 17A-17B, as with the laser-etched lines, square grid lines spaced by 0.5 mm provide a modest increase in average and maximum peel force over more widely spaced grid lines. The experimental average and maximum peel forces again are in good agreement with theoretical peel forces (shown as a dashed line) calculated according to the inverse cubic function.

For a given line spacing, grid lines provide increased exposure of the PET backing to the adhesive layer as compared to lines (i.e., $x_{lines}$ versus $x_{grid\ lines}$). Thus, as might be expected, grid lines spaced by 1 mm result in peel forces similar to peel forces of lines spaced by 0.5 mm, as these two geometries offer roughly equivalent amounts of exposed PET. Similarly, the 0.5 mm spaced grid lines cause a peel force of approximately double the peel force of the 0.5 mm spaced lines, because a greater amount of PET is exposed to the adhesive by the grid lines.

Figure 17C:
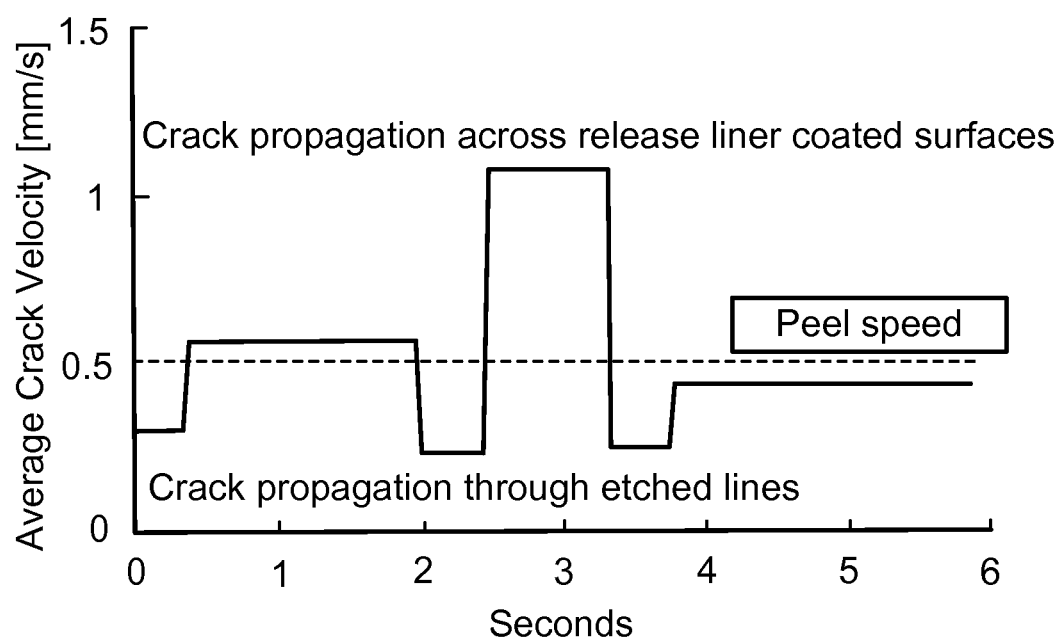
FIG. 17C is a plot of the average crack velocity as a function of time for crack propagation in different regions of a quick-release tape.

Referring to FIG. 17C, the mechanism of adhesion of a quick-release tape having release agent layers micro-patterned with 1 mm spaced laser-etched grid lines etching was studied using high-speed (100 Hz) video analysis of crack propagation. Peel tests (0.5 mm/s peel rate) were conducted and the rate of crack propagation was determined. Analysis of video images revealed that the rate of crack propagation was slower within regions where the adhesive layer contacts the PET backing and faster within regions where the release agent layer contacts the PET backing High-speed video was captured using Dino-Lite® Digital Microscope Pro using DinoCapture 2.0 software for image analysis. Individual frames were analyzed to track the propagation of the crack front as a function of time. Crack propagation rates perpendicular to the peel direction across release agent coated surfaces and within laser-etched lines were averaged separately to arrive at average crack propagation speeds for each region.

Example 7—Effect of Mechanical Abrasion of Release Agent Layer on Adhesion

Figure 18A:
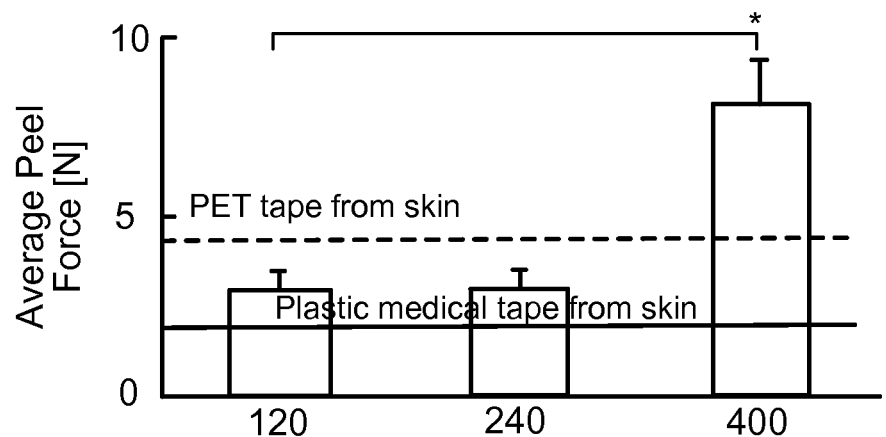
FIGS. 18A and 18B are plots of the average peel force and maximum peel force, respectively, as a function of the grit of sand paper used to roughen the release agent layer of a quick-release tape.
Figure 18B:
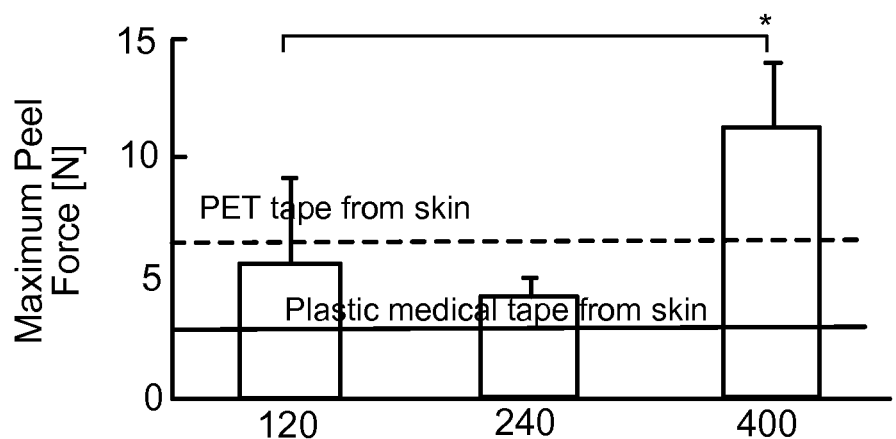

Referring to FIGS. 18A-18B, release agent layers coated on PET backings were mechanically abraded using sandpaper to create micro-scale divots in the release agent layers. An acrylic-based adhesive was solvent cast onto each mechanically patterned release agent layer to form a tape strip. Each tape strip was adhered to a stainless steel substrate and a 90 degree peel test was conducted to measure the average and maximum peel force.

The root mean square (RMS) average surface roughness created by sandpaper roughening, as measured via two-dimensional surface profilometry, of the release agent layer decreases with decreasing particle size, indicating that the morphology of the release agent layer is controllable via appropriate selection of sandpaper grit.

Release agent layers patterned with 120 grit sandpaper (115 μm average particle diameter) and 240 grit sandpaper (53 μm average particle diameter) resulted in similar peel forces (i.e., similar adhesion). While the grit is more densely packed on the 240 grit sandpaper than it is on the 120 grit sandpaper, the grit layer on the 120 grit sandpaper is thicker. Therefore, the 120 grit sandpaper creates deeper divots than the 240 grit sandpaper, likely causing similar amounts of PET to be exposed to the adhesive layer. The adhesive is sufficiently amorphous and viscous to be able to fill the micro-scale divots produced by sandpaper roughening of the release agent layer.

400 grit sandpaper (23 µm average particle diameter) results in a peel force that is significantly higher than the peel force associated with the larger grit sandpapers. Indeed, the peel force of tapes patterned with 400 grit sandpaper was so high that portions of the adhesive were removed from the stainless steel plate during the peel test. The average particle radius of 40 grit sandpaper (11.5 µm) is an order of magnitude larger than the thickness of the release agent layer (0.5-0.8 µm). Thus, abrasion with 400 grit sandpaper readily removes a large amount of PET, exposing a significant fraction of the PET backing to the adhesive layer. Without wishing to be bound by theory, it is expected that the large contact area between the PET backing and the adhesive layer stabilizes the interface between the adhesive layer and the support layer, causing the fracture zone to transition from that interface to the adhesive layer-substrate interface.

Example 9—Anisotropic Adhesion

The foregoing examples demonstrate that the adhesion of a quick-release tape can be controlled via structural manipulation of the release agent layer. However, in addition to the ability to achieve a target adhesion, it is desirable for a quick-release tape to have the ability to securely affix a device to a substrate. To demonstrate this functionality of the quick-release tape, a neonatal endotracheal (ET) tube, which is a tube commonly used to support respiratory function, was adhered to a substrate using a variety of medical tapes. The shear and normal adhesion of each tape to the substrate were measured.

An uncuffed neonatal ET tube 1900 (Smiths Medical, Norwell, Mass.) was affixed to a polished stainless steel plate 1904 by each of a quick-release tape having a sandpaper abraded release agent layer, commercially available plastic- and paper-backed medical tapes (3M™ Transpore™ Medical Tape and 3M™ Micropore™ Medical Tape, respectively); and NeoFlex™, a tape designed specifically for easy removal from neonates.

Figure 19A:
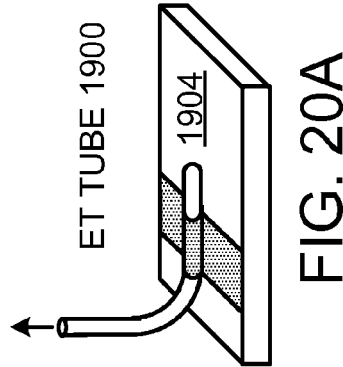
FIG. 19A is a schematic diagram of an experimental setup for a shear force test of an endotracheal (ET) tube attached to a substrate with quick-release tape.

Referring to FIG. 19A, to measure shear adhesion, one end of the ET tube was pulled parallel to the surface of the stainless steel plate and along a longitudinal axis of the tube at a rate of 5 mm/s while recording shear force as a function of pull distance. The maximum shear force was determined by identifying the maximum force reached during each test.

Figure 19B:
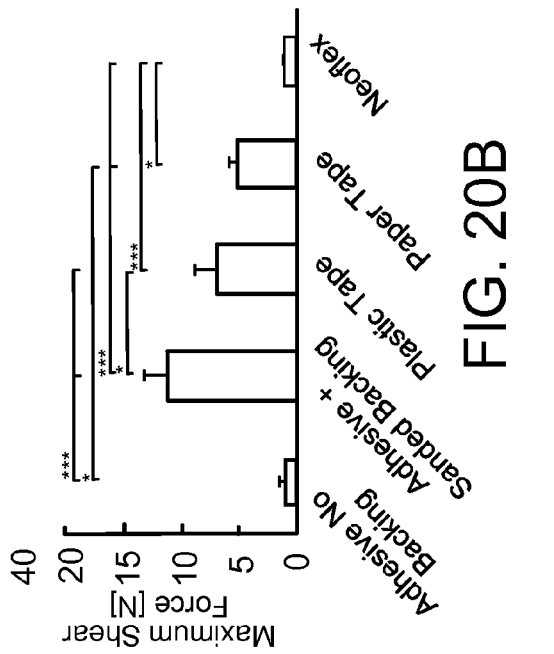
FIG. 19B is a plot of the results of the shear force test of FIG. 19A.

Referring to FIG. 19B, with the support layer in place, the quick-release tapes performed better than standard plastic- and paper-backed medical tapes, exhibiting higher average maximum shear force than both commercially available tapes. The difference in maximum shear force between intact quick-release tapes and the tested commercial tapes may be due to the use of a less aggressive adhesive in the commercial tapes. Quick-release tapes with the backing in place also significantly outperformed NeoFlex™.

Once the support layer is removed from the quick-release tapes, only the cohesive strength of the adhesive layer holds the ET tube in place. Cohesive failure involves minimal shear force; a drop of 83% in maximum shear force is measured compared to the shear force measured for intact quick-release tapes (i.e., a device fixation shear adhesion characteristic of the quick-release tape is reduced by removal of the support layer). The adhesive layer alone exhibits a similar average maximum shear force as NeoFlex™, which is designed specifically to have low adhesive strength to facilitate easy removal in a neonatal care situation.

Figure 20A:
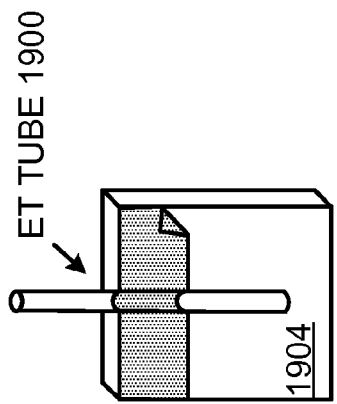
FIG. 20A is a schematic diagram of an experimental setup for a 90 degree peel test of an ET tube attached to a substrate with quick-release tape.

Referring now to FIG. 20A, to test device fixation in the normal (or perpendicular) direction, one end of the ET tube was lifted upwards and away from the stainless steel plate at 5 mm/s at a 90 degree angle until adhesive bond failure occurred. The force was continually monitored during the test. The maximum peel force was determined by identifying the maximum force reached during each test.

Figure 20B:
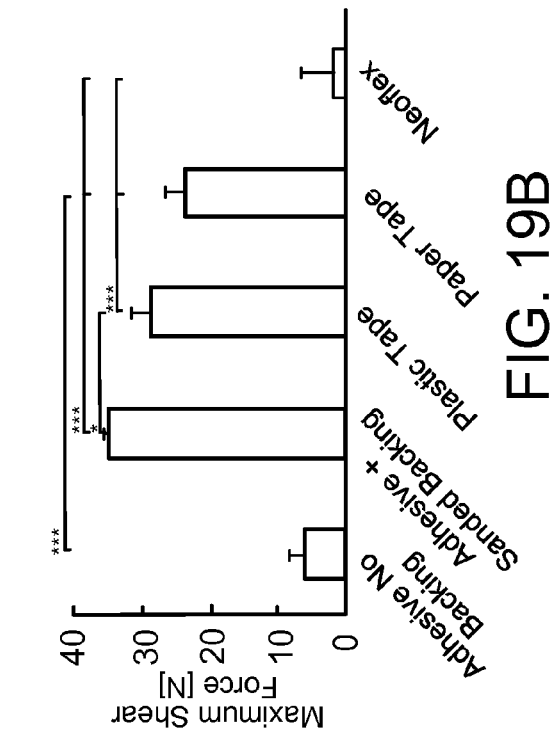
FIG. 20B is a plot of the results of the peel test of FIG. 20A.

Referring to FIG. 20B, intact quick-release tapes exhibited the highest maximum normal peel force, followed by commercial plastic- and paper-backed medical tapes. NeoFlex™ and the residual adhesive from the quick-release tapes demonstrated the lowest normal peel forces. In particular, after removal of the support layer of the quick-release tapes, the residual adhesive exhibited a maximum normal peel force 93% lower than intact quick-release tapes, demonstrating the ability of quick-release tapes to facilitate quick, damage-free device removal.

By comparing the maximum shear performance (FIG. 19B) and the backing peel force (FIGS. 16A-16B, 17A-17B, and 18A-18B) of the quick-release tapes, the directional anisotropy in the adhesion between the adhesive layer and the support layer is apparent. That is, intact quick-release tapes provide significant adhesion in shear between the adhesive layer and the support layer. However, the support layer exhibits minimal adhesion to the adhesive layer when peeled normally from the adhesive layer.

Example 10—Strength and Quantity of Residual Adhesive

Referring to FIG. 21A, a probe tack test was used to measure the maximum tensile strength adhering a probe to a surface. Probe tack tests were used to characterize a layer of adhesive meant to correspond to residual adhesive remaining on a surface after removal of the support layer of a quick-release tape. An acrylic-based adhesive 2100 was adhered to a flat aluminum sheet 2102. A 1 cm diameter aluminum probe 2104 was positioned parallel to the aluminum sheet and brought into contact with adhesive 2000 at a speed of 1 mm/s until reaching a target compressive force of 3 N. The probe was allowed to dwell in contact with the adhesive for 30 seconds, and was then pulled away at a speed of 1 mm/s while monitoring the tack force as a function of distance. The tensile fracture strength of the adhesive was calculated as the maximum tack force measured during each test, normalized to the cross-sectional area of the probe (0.8 cm$^2$).

After the probe tack test of the adhesive was conducted, talcum ("baby") powder (Johnson & Johnson, New Brunswick, N.J.) was applied to the exposed adhesive surface. A probe tack test was conducted on the talc-fouled adhesive. The talc-fouled adhesive was then immersed in water to remove the excess powder and dried; a probe tack test was conducted on the washed, talc-fouled adhesive. Finally, a layer of the same adhesive was applied directly onto probe 2104 and the probe tack test was repeated on the washed, talc-fouled residual adhesive 2100.

Referring to FIG. 21B, pristine residual adhesive has an average tensile fracture strength of 4.1±0.3 N/cm$^2$. Fouling the residual adhesive with talcum powder effectively detackifies the adhesive, reducing the average tensile fracture strength by 97.6%, to $0.01\pm0.1$ N/cm$^2$.

Referring to FIG. 21C, washing away the excess talcum powder leaves a thin layer of adhered talc particles, which is translucent and permits visual inspection of the underlying adhesive surface. A probe tack test to the washed (and dried), talc-fouled adhesive reveals a low tensile fracture strength on the order of the tensile fracture strength of the unwashed, talc-fouled adhesive, demonstrating that immersion in water does not affect the talc-fouling of the residual adhesive.

A second adhesive adhered to the washed, talc-fouled adhesive effectively recovers the full tensile fracture strength ($3.7\pm0.8$ N/cm$^2$) of the adhesive to the probe, demonstrating that the de-tackified adhesive can serve as a fixation point for future adhesives.

The residual adhesive remaining after removal of the backing or support layer of a tape can be quantified. Plastic- and paper-backed commercial medical tapes (3M™ Micropore™ Medical Tape and 3M™ Transpore™ Medical Tape, respectively) were tested and compared with quick-release tapes having a 45 μm thick adhesive layer with a coating weight of either 1 mil or 1.8 mil. The commercial medical tapes had an adhesive layer approximately 25 μm thick. To measure the residual adhesive, 44 cm strips of each tape were applied to pre-weighed pieces of aluminum foil using a 10-pound hand roller (ChemInstruments, Fairfield, Ohio). The tape strips were rapidly removed and the aluminum foil sheets weighed. The increase in mass of the aluminum foil was normalized to the cross-sectional area of the applied tape to yield values of residual adhesive mass per square centimeter.

Paper-backed tape left more residual adhesive per square centimeter than plastic-backed tape. Patterned quick-release tapes left the entire adhesive layer on the aluminum foil, yielding more residual adhesive than commercial tapes consistent with the coating weight of the adhesive layer. In practice, this result suggests that when designing a quick-release tape an adhesive can be chosen having a desired adhesion to a target substrate and a coating thickness such that the mass per unit area of the residual adhesive can match that of a conventional commercial tape.

Example 8—Use of Commercially Available Materials for Quick-Release Tapes

PET is often used as a test backing for medical tapes (e.g., for the foregoing examples) and for transfer film construction. However, PET is a non-standard commercial medical tape backing. To demonstrate the generalizability of the approach of micro-patterning a release agent layer to form a quick-release tape, a quick-release tape was constructed using a commonly used commercial backing.

Commercially available plastic-backed tape (3M™ Transpore™ Medical Tape) has a backing composed of a proprietary polyethylene-ethylene vinyl acetate blend (PE/EVA). PE/EVA tape was soaked in ethanol for 12 hours to swell the adhesive layer, which was then removed with mechanical abrasion, leaving only the backing. The PE/EVA backing was coated in release agent, which was micro-patterned via mechanical abrasion with 240 grit sandpaper to expose regions of the underlying PE/EVA backing. The acrylic-based adhesive layer used in the foregoing examples was disposed on the release agent layer. 90 degree peel tests were conducted for the original, commercially available PE/EVA backed tape (PE/EVA); a PE/EVA backed tape with an unpatterned release agent layer, and a micro-patterned PE/EVA tape to measure average and maximum peel forces for each tape from a stainless steel substrate.

Figure 22:
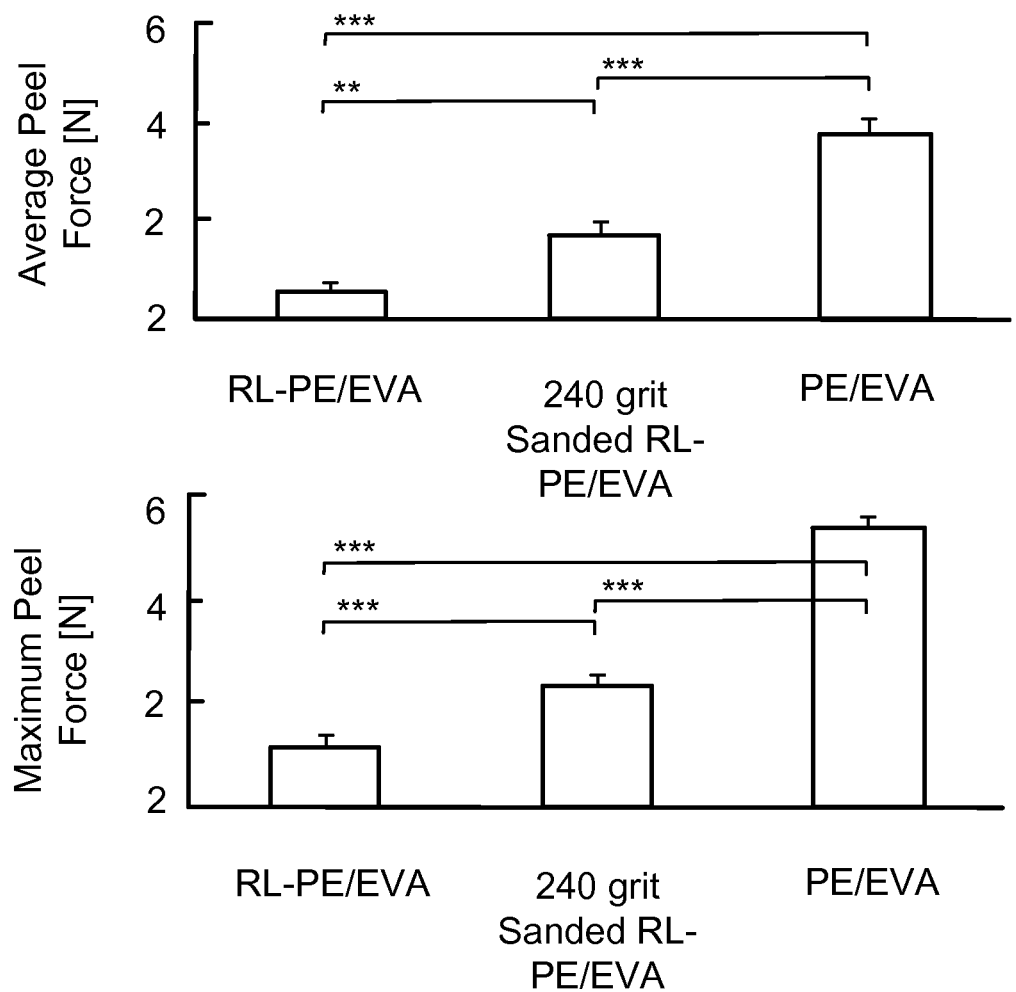
FIG. 22 is a plot of the average peel force and maximum peel force, respectively, for alternative backings for a quick-release tape.

Referring to FIG. 22, the micro-patterned release agent layer coated PE/EVA tape exhibited a peel force between the values obtained for unpatterned release agent layer coated PE/EVA tape and commercially available PE/EVA tape. The overall trend of a decrease in peel force with an increase in percent area of exposed backing is maintained. That is, the support layer peel force can be tuned via micro-patterning of the release agent layer, regardless of the composition of the support layer (and specifically, the composition of the backing).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A quick-release tape comprising:
   a support layer, comprising:
      a backing layer, and
      a patterned release agent layer disposed on a first side of the backing layer;
   an adhesive layer disposed on the release agent layer; and
   an antiadhesive cover layer in contact with the support layer,
   wherein the tape is provided in a roll such that in the roll, the cover layer is in contact with a second side of the backing layer,
   wherein an adhesion level between the cover layer and the support layer is less than an adhesion level between the adhesive layer and the support layer, and
   wherein the adhesion level between the adhesive layer and the support layer is greater than an adhesion level between the adhesive layer and the cover layer.

2. The tape of claim 1, wherein when the adhesive layer is disposed on a substrate, a first adhesion level between the adhesive layer and the substrate is greater than a second adhesion level between the adhesive layer and the support layer.

3. The tape of claim 1, wherein an adhesion level between the adhesive layer and the release agent layer is a function of an angle of a force applied to an interface between the adhesive layer and the release agent layer.

4. The tape of claim 1, wherein the release agent layer includes first domains and second domains.

5. The tape of claim 4, wherein a first adhesion level between the first domains and the adhesive layer is different from a second adhesion level between the second domains and the adhesive layer.

6. The tape of claim 4, wherein an adhesion level between the adhesive layer and the support layer is a function of a fraction of the area of the release agent layer composed of the first domains.

7. A quick-release tape comprising:
   a support layer, comprising:
      a backing, and
      a release agent layer disposed on a first side of the backing layer;
   an adhesive layer disposed on the release agent layer; and
   an antiadhesive cover layer in contact with the support layer, wherein the tape is provided in a roll such that in the roll, the cover layer is in contact with a second side of the backing layer, wherein an adhesion level between the cover layer and the support layer is less than an adhesion level between the adhesive layer and the support layer, wherein the adhesion level between the adhesive layer and the support layer is greater than an adhesion level between the adhesive layer and the cover layer, and wherein the release agent layer is formed of a material having an adhesion level that changes in response to a stimulus.

8. The tape of claim 1, wherein the cover layer is disposed on the adhesive layer.

* * * * *

UNITED STATES PATENT AND TRADEMARK OFFICE
CERTIFICATE OF CORRECTION

PATENT NO. : 9,907,704 B2
APPLICATION NO. : 14/405917
DATED : March 6, 2018
INVENTOR(S) : Bryan Laulicht, Jeffrey M. Karp and Robert S. Langer Page 1 of 1

It is certified that error appears in the above-identified patent and that said Letters Patent is hereby corrected as shown below:

On the Title Page

On Line 1 of item (71), delete "Women s" and insert -- Women's --

Signed and Sealed this
Eleventh Day of December, 2018

Andrei Iancu
*Director of the United States Patent and Trademark Office*